US008647874B2

(12) United States Patent
Offen et al.

(10) Patent No.: US 8,647,874 B2
(45) Date of Patent: *Feb. 11, 2014

(54) ISOLATED CELLS AND POPULATIONS COMPRISING SAME FOR THE TREATMENT OF CNS DISEASES

(75) Inventors: Daniel Offen, Kfar HaRoe (IL); Merav Bahat-Stromza, Herzlia (IL); Eldad Melamed, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1307 days.

This patent is subject to a terminal disclaimer.

(21) Appl. No.: 11/727,583

(22) Filed: Mar. 27, 2007

(65) Prior Publication Data
US 2009/0010895 A1   Jan. 8, 2009

Related U.S. Application Data

(63) Continuation-in-part of application No. PCT/IL2006/000699, filed on Jun. 18, 2006.

(60) Provisional application No. 60/690,879, filed on Jun. 15, 2005.

(51) Int. Cl.
*C12N 5/00* (2006.01)

(52) U.S. Cl.
USPC ........... 435/377; 435/375; 435/325; 424/93.7

(58) Field of Classification Search
None
See application file for complete search history.

(56) References Cited

U.S. PATENT DOCUMENTS

| | | | |
|---|---|---|---|
| 5,229,500 A * | 7/1993 | Barde et al. ..................... 514/12 |
| 5,464,764 A | 11/1995 | Capecchi et al. | |
| 5,487,992 A | 1/1996 | Capecchi et al. | |
| 5,780,587 A * | 7/1998 | Potter ............................ 530/326 |
| 5,830,621 A | 11/1998 | Suzuki et al. | |
| 5,968,829 A | 10/1999 | Carpenter | |
| 6,528,245 B2 | 3/2003 | Sanchez-Ramos et al. | |
| 6,576,464 B2 | 6/2003 | Gold et al. | |
| 6,989,271 B2 | 1/2006 | Dezawa et al. | |
| 2002/0009743 A1 * | 1/2002 | Carpenter ........................ 435/6 |
| 2002/0081724 A1 | 6/2002 | Carpenter et al. | |
| 2002/0146821 A1 | 10/2002 | Sanchez-Ramos et al. | |
| 2004/0208858 A1 | 10/2004 | Tennekoon et al. | |
| 2005/0265983 A1 | 12/2005 | Melamed et al. | |
| 2006/0166362 A1 | 7/2006 | Dezawa et al. | |
| 2012/0009673 A1 | 1/2012 | Kadouri et al. | |
| 2013/0236964 A1 | 9/2013 | Melamed et al. | |

FOREIGN PATENT DOCUMENTS

| | | |
|---|---|---|
| AU | 2003207064 | 9/2003 |
| WO | WO 97/32608 | 9/1997 |
| WO | WO 99/43286 | 2/1999 |
| WO | WO 99/56759 | 11/1999 |
| WO | WO 01/11011 | 2/2001 |
| WO | WO 01/88104 | 11/2001 |
| WO | WO 02/064748 | 8/2002 |
| WO | WO 02/086108 | 10/2002 |
| WO | WO 03/059272 | 7/2003 |
| WO | WO 2004/046348 | 6/2004 |
| WO | WO 2006/134602 | 12/2006 |
| WO | WO 2007/066338 | 6/2007 |
| WO | WO 2009/144718 | 12/2009 |

OTHER PUBLICATIONS

Dezawa et al, 2001. Sciatic nerve regeneration in rat induced by transplantation of in vitro differentiated bone-marrow stromal cells. European Journal of Neuroscience, vol. 14:1771-1776.*
Levy et al, 2003. Induction of neuron-specific enolase promoter and neuronal markers in differentiated mouse bone marrow stromal cells. Journal of Molecular Neuroscience, vol. 21:121-132; provided by applicant on the Jan. 23, 2008 IDS.*
Saitoh F et al. 2010. Proteasomal degradation of glutamine synthetase regulates schwann cell differentiation. J Neurosci 30: 1204-1212. Abstract only.*
Carozzi VA et al. 2008. Expression and distribution of 'high affinity' glutamate transporters GLT1, GLAST, EAAC1 and of GCPII in the rat peripheral nervous system. J Anat 213: 539-546.*
Ohishi M et al. 2009. GDNF expression in terminal schwann cells associated with the periodontal ruffini endings of the rat incisors during nerve regeneration. Anat Rec 292: 1185-1191. Abstract only.*
Tohill M et al. 2004. Rat bone marrow mesenchymal stem cells express glial markers and stimulate nerve regeneration. Neurosci Lett 362: 200-203.*
Keilhoff G et al. 2006. Transdifferentiation of mesenchymal stem cells into Schwann cell-like myelinating cells. Eur J Cell Biol 85: 11-24.*
Magaki T et al. 2005. Generation of bone marrow-derived neural cells in serum-free monolayer culture. Neurosci Lett 384: 282-287.*
Invitrogen. "Technical Resources—Media Formulations: N-2 Supplement (100x) Liquid." Available online at <http://www.lifetechnologies.com/us/en/home/technical-resources/media-formulation.166.html>. Accessed Sep. 27, 2013.*
Bossolasco P et al. 2005. Neuro-glial differentiation of human bone marrow stem cells in vitro. Exp Neurol 193: 312-325.*
Yarowsky PJ et al. 1989. Development of Saxitoxin-Sensitive and Insensitive Sodium Channels in Cultured Neonatal Rat Astrocytes. J Neurosci 9: 1055-1061.*
Aldous et al. "Fresh Questions on Stem Cell Findings", New Scientist Magazine, 2596: 12-13, 2007.
Bendotti et al. "Transgenic SOD1 G93A Mice Develop Reduced GLT-1 in Spinal Cord Without Alterations in Cerebrospinal Fluid Glutamate Levels", Journal of Neurochemistry, 79: 737-746, 2001.
Black et al. "Adult Rat and Human Bone Marrow Stromal Stem Cells Differentiate Into Neurons", Blood Cells, Molecules, and Diseases, 27(3): 632-636, 2001.
Canaple et al. "Improving Cell Encapsulation Through Size Control", Journal of Biomaterials Science, Polymer Edition, 13(7): 783-796, 2002.

(Continued)

Primary Examiner — Lora E Barnhart Driscoll

(57) ABSTRACT

An isolated human cell and populations thereof is provided comprising at least one astrocytic phenotype and at least one mesenchymal stem cell phenotype, wherein the mesenchymal stem cell phenotype is not an astrocytic phenotype.

14 Claims, 23 Drawing Sheets

(56) References Cited

OTHER PUBLICATIONS

Chang et al. "Procedures for Microencapsulation of Enzymes, Cells and Genetically Engineered Microorganisms", Molecular Biotechnology, 17: 249-260, 2001.
Check "The Hard Copy", Nature, 446: 485-486, 2007.
Chia et al. "Multi-Layered Microcapsules for Cell Encapsulation", Biomaterials, 23: 849-856, 2002.
Deng et al. "In Vitro Differentiation of Human Marrow Stromal Cells Into Early Progenitors of Neural Calls by Conditions That Increase Intracellular Cyclic AMP", Biochemical and Biophysical Research Communications, 282: 148-152, 2001.
Desai "Microfabrication Technology for Pancreatic Cell Encapsulation", Expert Opinion on Biological Therapy, 2(6): 633-646, 2002.
Garcia et al. "Bone Marrow Stromal Cells Produce Nerve Growth Factor and Glial Cell Line-Derived Neurotrophic Factors", Biochemical and Biophysical Research Communications, 316: 753-754, 2004.
Jiang et al. "Pulripotency of Mesenchymal Stem Cells Derived From Adult Marrow" Nature, 418, 41-49, 2002.
Kafri et al. "Lentiviral Vectors: Regulated Gene Expression", Molecular Therapy, 1(6): 516-521, 2000.
Kan et al. "Integral Therapeutic Potential of Bone Marrow Mesenchymal Stem Cells", Current Drug Targets, 6:31-41, 2005.
Kandel et al. Principles of Neural Science, 3rd Edition (26): 367-384.
Kassis et al. "Isolation of Mesenchymal Stem Cells From G-CSF-Mobilized Human Peripheral Blood Using Fibrin Microbeads", Bone Marrow Transplantation, 37: 967-976, 2006.
Kern et al. "Comparative Analysis of Mesenchymal Stem Cells From Bone Marrow, Umbilical Cord Blood, or Adipose Tissue", Stem Cells, 24: 1294-1301, 2006.
Kohyama et al. "Brain From Bone: Efficient 'Meta-Differentiation' of Marrow Stroma-Derived Mature Osteoblasts to Neurons With Noggin or A Demethylating Agent", Differentiation, 68: 235-244, 2001.
Kopen et al. "Marrow Stromal Cells Migrate Throughout Forebrain and Cerebellum, and They Differentiate Into Astrocytes After Injection Into Neonatal Mouse Brains", Proc. Natl. Acad. Sci. USA, 96: 10711-10716, 1999.
Levy et al. "Embryonic and Adult Stem Cells as a Source for Cell Therapy in Parkinson's Disease", Journal of Molecular Neuroscience, 24: 353-385, 2004.
Levy et al. "Induction of neuron-Specific Enolase Promoter and Neuronal Markers in Differentiated Mouse Bone Marrow Stromal Cells", Journal of Molecular Neuroscience, 21: 121-132, 2003.
Li et al. "Intracerebral Transplantatidn of Bone Marrow Stromal Cells in A 1-Methyl-4-Phenyl-,-1,2,3,6-Tetrahydropyridine Mouse Model of Parkinson's Disease", Neuroscience Letters, 316(2): 67-70, 2001.
Li et al. "Intrastriatal Transplantation of Bone Marrow Nonhematopoietic Cells Improves Functional Recovery After Stroke in Adult Mice", Journal of Cerebral Blood Flow and Metabolism, 20: 1311-1319, 2000.
Lu et al. "A Novel Cell Encapsulation Method Using Photosensitive Poly(Allylamine α-Cyanocinnam Ylideneacytate)", Journal of Microencapsulation, 17(2): 245-251, 2000.
Lu et al. "Cell Encapsulation With Alginate and α-Phenoxycinnamylidene-Acetylated Poly(Allylamine)", Biotechnology and Bioengineering, 70: 479-483, 2000.
Mahmood et al. "Treatment of Traumatic Brain Injury in Female Rats With Intravenous Administration of Bone Marrow Stromal Cells", Neurosurgery, 49: 1196-1204, 2001.
Mehta et al. "Graft Survival", Journal of Neurosurgery, 90: 804-806, 1999.
Park et al. "Protection of Nigral Neurons by GDNF-Engineered Marrow Cell Transplantation", Neuroscience Research, 40: 315-323, 2001.
Rendahl et al. "Regulation of Gene Expression in Vivo Following Transduction by Two Separate Raav Vectors", Nature Biotechnology, 16: 757-761, 1998.

Reyes et al. "Characterization of Multipotent Adult Progenitor Cells, A Subpopulation of Mesenchymal Stem Cells", Annals of the New York Academy of Sciences, 938: 231-235, 2001.
Reynolds et al. "A Multipotent EGF-Responsive Striatal Embryonic Progenitor Cell Produces Neurons and Astrocytes", The Journal of Neuroscience, 12(11): 4565-4574, 1992.
Reynolds et al. "Generation of Neurons and Astrocytes From Isolated Cells of the Adult Mammalian Central Nervous System", Science, 255: 1707-1710, 1992.
Sambanis "Encapsulated Islets in Diabetes Treatment", Diabetes Technology & Therapeutics, 5(4): 665-668, 2003.
Sanchez-Ramos et al. "Adult Bone Marrow Stromal Cells Differentiate Into Neural Cells in Vitro", Experimental Neurology, 164: 247-256, 2000.
Schwarz et al. "Multipotential Marrow Stromal Cells Transduced to Produce L-DOPA: Engraftment in a Rat Model of Parkinson Disease", Human Gene Therapy, 10(15): 2539-2549, 1999. p. 2542-2544, p. 2546-2548.
Schwarz et al. "Rat Marrow Stromal Cells Rapidly Transduced With a Self-Inactivating Retrovirus Synthesize L-DOPA in Vitro", Gene Therapy, 8(16); 1214-1223, 2001. p. 1215, p. 1218, p. 1219-1220.
Stenevi et al. "Transplantation of Central and Peripheral Monoamine Neurons to the Adult Rat Brain: Techniques and Conditions for Survival", Brain Research, 114: 1-20, 1976.
Uludag et al. "Technology of Mammalian Cell Encapsulation", Advanced Drug Delivery Reviews, 42: 29-64, 2000.
Williams "Small is Beautiful: Microparticle and Nanoparticle Technology in Medical Devices", Medical Device Technology, 10: 6-9, 1999.
Woodbury et al. "Adult Bone Marrow Stromal Stem Cells Express Germline, Ectodermal, Endodermal, and Mesodermal Genes Prior to Neurogenesis", Journal of Neuroscience Research, 96: 908-917, 2002.
Woodbury et al. "Adult Rat and Human Bone Marrow Stromal Cells Differentiate Into Neurons", Journal of Neuroscience Research, 61: 364-370, 2000.
Zhang et al. "Comparison of Mesenchymal Stem Cells from Human Placenta and Bone Marrow", Chinese Medical Journal, 117(6): 882-887, 2004.
Ikemoto et al. "Membrane Fatty Acid Modifications of PC12 Cells by Arachidonate or Docosahexaenoate Affect Neurite Outgrowth But Not Norephinephrine Release", Neurochemical Research, 22(6): 671-678, 1997.
Blondheim et al. "Human Mesenchymal Stem Cells Express Neural Genes, Suggesting a Neural Predisposition", Stem Cells and Development, 15(2): 141-164, 2006.
Brierley et al. "Remyelination of Demyelinated CNS Axons by Transplanted Human Schwann Cells: the Deleterious Effect of Contaminating Fibroblasts",Cell Transplant, 10(3): 305-315, 2001.
Kohama et al. "Transplantation of Cryopreserved Adult Human Schwann Cells Enhances Axonal Conduction in Demyelinated Spinal Cord", Journal of Neuroscience, 21(3): 944-950, Feb. 2001.
Lee et al. "Migration and Differentiation of Nuclear Fluorescence-Labeled Bone Marrow Stromal Cells After Transplantation Into Cerebral Infarct and Spinal Cord Injury in Mice", Neuropathology, 23(3): 169-180, Sep. 2003. Abstract.
Raff "Glial Cell Diversification in the Rat Optic Nerve", Science, 243(4897): 1450-1455, Mar. 1989. Abstract.
Reyes "Turning Marrow Into Brain: Generation of Glial and Neuronal Cells From Adult Bone Marrow Mesenchymal Stem Cells", Blood, 94(10): 377A, 1999. Abstract. Abstract.
Sasaki et al. "Transplantation of an Acutely Isolated Bone Marrow Fraction Repairs Demyelinated Adult Rat Spinal Cord Axons", GLIA, 35: 26-34, 2001.
Tondreau et al. "Bone Marrow-Derived Mesenchymal Stem Cells Already Express Specific Neural Proteins Before Any Differentiation", Differentiation, 72(7): 319-326, 2004. p. 320, r-h Col., Paragraph 3.
Munoz et al. "Human Adult Stem Cells From Bone Marrow Stroma Express Trophic factors in Culture and Following Transplantation in Brain", Society for Neuroscience Abstract Viewer and Itinerary Planner, 2003: 300.16, 2003. Abstract. & 33rd Annual Meeting of the Society of Neuroscience, New Orleans, LA, USA, Nov. 8-12, 2003.

(56) References Cited

OTHER PUBLICATIONS

Dormady et al. "Immortalized Multipotential Mesenchymal Cells and the Hematopoietic Microenvironment", Journal of Hematotherapy & Stem Cell Research, 10: 125-140, 2001. p. 125, p. 134-138.
Examination Report Dated Oct. 13, 2008 From the Intellectual Property Office of New Zealand Re.: Application No. 564745.
Examiner's Report Dated Mar. 6, 2008 From the Australian Government, IP Australia Re.: Application No. 2005202128.
Official Action Dated Aug. 7, 2009 From the US Patent and Trademark Office Re.: U.S. Appl. No. 11/130,197.
Response Dated Dec. 28, 2009 to Official Action of Aug. 7, 2009 From the US Patent and Trademark Office Re.: U.S. Appl. No. 11/130,197.
Supplemental Response Dated Feb. 24, 2010 to Official Action of Aug. 7, 2009 From the US Patent and Trademark Office Re.: U.S. Appl. No. 11/130,197.
Bourre et al. "Effect of Polyunsaturated Fatty Acids on Fetal Mouse Brain Cells in Culture in a Chemically Defined Medium", Journal of Neurochemistry, 41: 1234-1242, 1983.
Official Action Dated Apr. 15, 2010 From the US Patent and Trademark Office Re.: U.S. Appl. No. 11/130,197.
Response Dated May 3, 2010 to Official Action of Apr. 15, 2010 From the US Patent and Trademark Office Re.: U.S. Appl. No. 11/130,197.
Communication Pursuant to Article 94(3) EPC Dated Jun. 10, 2010 From the European Patent Office Re.: Application No. 06766101.7.
Padovan et al. "Expression of Neuronal Markers in Differentiated Marrow Stromal Cells and CD133+ Stem-Like Cells", Cell Transplantation, XP009117445, 12: 839-848, 2003.
Tohill et al. "Rat Bone Marrow Mesenchymal Stem Cells Express Glial Markers and Stimulate Nerve Regeneration", Neuroscience Letters, 362: 200-203, 2004.
Wislet-Gendebien et al. Astrocytic and Neuronal Fate of Mesenchymal Stem Cells Expressing Nestin, Brain Research Bulletin, 68: 95-102, 2005.
Examiner's Report Dated Aug. 25, 2010 From the Australian Government, IP Australia Re. Application No. 2007201401.
Official Action Dated Dec. 7, 2011 From the US Patent and Trademark Office Re.: U.S. Appl. No. 11/130,197.
Lu et al. "induction of Bone Marrow Stromal Cells to Neurons: Differentiation, Transdifferentiation, or Artifact?", Journal of Neuroscience Research, 77: 174-191, 2004.
Moore "Polyunsaturated Fatty Acid Synthesis and Release by Brain-Derived Cells In Vitro", Journal of Molecular Neuroscience, 16: 195-200, 2001.
Moore et al. "Astrocytes, Not Neurons, Produce Docosahexaenoic Acid (22:6Omega-3) and Arachidonic Acid (20:4Omega-6)", Journal of Neurochemistry, 56: 518-524, 1991.
Official Action Dated Jan. 20, 2012 From the US Patent and Trademark Office Re. U.S. Appl. No. 12/085,995.
Goodwin et al. "Multilineage Differentiation Activity by Cells Isolated From Umbilical Cord Blood: Expression of Bone, Fat, and Neural Markers", Biology of Blood and Marrow Transplantation, 7: 581-588, 2001.
Official Action Dated Mar. 11, 2013 From the US Patent and Trademark Office Re. U.S. Appl. No. 12/994,761.
Jones et al. "Human Neutrotrophin-3 (NT-3) Gene, Complete CDS", Database NCBI [Online], GenBank: M37763.1, GenBank Accession No. M37763, Jan. 7, 1995.
Kaisho et al. "Nerve Growth Factor [*Homo sapiens*]", NGF Database [Online], GenBank: CAA37703.1, GenBank Accession No. CAA37703, Mar. 11, 1993.
Kurozumi et al. "BDNF Gene-Modified Mesenchymal Stem Cells Promote Functional Recovery and Reduce Infarct Size in the Rat Middle Cerebral Artery Occlusion Model", Molecular Therapy, 9(2): 189-197, Feb. 2004.
Official Action Dated Apr. 18, 2012 From the US Patent and Trademark Office Re.: U.S. Appl. No. 11/130,197.

Communication Pursuant to Article 94(3) EPC Dated Mar. 8, 2007 From the European Patent Office Re.: Application No. 03811473.2.
Communication Pursuant to Article 96(2) EPC Dated Nov. 18, 2005 From the European Patent Office Re.: Application No. 03811473.2.
International Preliminary Report on Patentability Dated Dec. 9, 2010 From the International Bureau of WIPO Re. Application No. PCT/IL2009/000525.
Response Dated Nov. 23, 2010 to Communication Pursuant to Article 94(3) EPC of Jun. 10, 2010 From the European Patent Office Re.: Application No. 06766101.7.
Written Opinion Dated Feb. 11, 2006 From the Intellectual Property Office of Singapore Issued by the Australian Patent Office Re.: Application No. SG 200503090-3.
Written Opinion Dated Oct. 24, 2006 From the Intellectual Property Offfice of Singapore Issued by the Australian Patent Office Re.: Applicaiton No. 200503090-3.
Blondheim et al. "Human Mesenchymal Stem Cells Express Neural Genes, Suggesting a Neural Predisposition", Stem Cells and Development, XP009079870, 15(2): 141-164, Apr. 2006.
Bossolasco et al. "Neuro-Glial Differentiation of Human Bone Marrow Stem Cells in Vitro", Experimental Neurology, 193(2): 312-325, Feb. 17, 2005. Abstract, p. 313, Left Col. 'Materials and Methods'— p. 320, Left Col., 2nd §, All Figs., p. 320, r-h Col., Lines 4-8, Fig.6, Table 1a, p. 321, r-h Col., Paragraph 3.
Farlie et al. "Bcl-2 Transgene Expression Can Protect Neurons Against Developmental and Induced Cell Death", Proc. Natl. Acad. Sci. USA, 92: 4397-4401, May 1995.
Garc?a et al. "Bone Marrow Stromal Cells Produce Nerve Growth Factor and Glial Cell Line-Derived Neurotrophic Factors", Biochemical and Biophysical Research Communications, 316: 753-754, 2004.
Lu et al. "A Novel Cell Encapsulation Method Using Photosensitive Poly(Allylamine ?-Cyanocinnam Ylideneacytate)", Journal of Microencapsulation, 17(2): 245-251, 2000.
Lu et al. "Cell Encapsulation With Alginate and ?-Phenoxycinnamylidene-Acetylated Poly(Allylamine)", Biotechnology and Bioengineering, 70: 479-483, 2000.
Munoz et al. "Human Adult Stem Cells From Bone Marrow Stroma Express Trophic Factors in Culture and Following Transplantation in Brain", Society for Neuroscience, Abstract Viewer and Itinerary Planner, 2003: Abstract No. 300.16, 2003. Abstract. & 33rd Annual Meeting of the Society of Neuroscience, New Orleans, LA, USA, Nov. 8-12, 2003.
Suzuki et al. "Neurospheres Induced From Bone Marrow Stromal Cells Are Multipotent for Differentiation Into Neuron, Astrocyte, and Oligodendrocyte Phenotypes", Biochemical and Biophysical Research Communications, 322(3): 918-922, Sep. 2004. Abstract.
Official Action Dated Jun. 6, 2012 From the US Patent and Trademark Office Re. U.S. Appl. No. 12/085,995.
Brüstle et al. "Embryonic Stem Cell-Derived Glial Precursors: A Source of Myelinating Transplants", Science, 285(5428): 754-756, Jul. 30, 1999.
Schuldiner et al. "Effects of Eight Growth Factors on the Differentiation of Cells Derived From Human Embryonic Stem Cells", Proc. Natl. Acad. Sci. USA, PNAS, 97(21): 11307-11312, Oct. 10, 2000.
Communciation Pursuant to Article 94(3) EPC Dated Mar. 8, 2007 From the European Patent Office Re.: Application No. 03811473.2.
Office Action Dated Aug. 14, 2012 From the Israel Patent Office Re. Application No. 209604 and Its Translation Into English.
Restriction Official Action Dated Oct. 11, 2012 From the US Patent and Trademark Office Re. U.S. Appl. No. 12/944,761.
Applicant-Initiated Interview Summary Dated Oct. 15, 2012 From the US Patent and Trademark Office Re. U.S. Appl. No. 11/130,197.
Restriciton Official Action Dated Nov. 9, 2011 From the US Patent and Trademark Office Re. U.S. Appl. No. 12/085,995.
Chu et al. "Signalling Pathway in the Induction of Neurite Outgrowth in Human Mesenchymal Stem Cells", Cellular Signalling, 18: 519-530, 2006.
Communication Pursuant to Article 94(3) EPC Dated Nov. 27, 2012 From the European Patent Office Re.: Application No. 06766101.7.
European Search Report and the European Search Opinion Dated Dec. 3, 2012 From the European Patent Office Re. Application No. 11000994.1.

(56) References Cited

OTHER PUBLICATIONS

Bahat-Stroomza et al. "Induction of Adult Human Bone Marrow Mesenchymal Stromal Cells Into Functional Astrocyte-Like Cells: Potential for Restorative Treatment in Parkinson's Disease", Journal of Molecular Neuroscience, XP009164575, 39(1-2): 199-210, Sep. 2009.

Deng et al. "Mesenchymal Stem Cells Spontaneously Express Neural Proteins in Culture and Are Neurogenic After Transplantation", Stem Cells, XP009164563, 24(4): 1054-1064, Apr. 1, 2006. p. 1057-1058.

Kramer et al. "Adult Rat Bone Marrow Stromal Cells Express Genes Associated With Dopamine Neurons", Biochemical and Biophysical Research Communications, XP024924814, 343(4): 1045-1052, May 19, 2006.

Official Action Dated Dec. 4, 2012 From the US Patent and Trademark Office Re.: U.S. Appl. No. 11/130,197.

Burchill et al. "Neuroblastoma Cell Detection by Reverse Transcriptase-Polymerase Chain Reaction (RT-PCR) for Tyrosine Hydroxylase mRNA", International Journal of Cancer, 57: 671-675, 1994.

Burdge et al. "Effect of Fatty Acid Supplementation on Growth and Differentiation of Human IMR-32 Neuroblastoma Cells in Vitro", Journal of Cellular Biochemistry, 80: 266-273, 2000.

Kan et al. "Docosahexaenoic Acid and Arachidonic Acid Are Fundamental Supplements for Induction of Neuronal Differentiation", Journal of Lipid Research, 55: 1-18, 2007.

Kirsch et al. "Characterization and Intracellular Distribution of Microtubule-Associated Protein 2 in Differentiating Human Neuroblastoma Cells", Journal of Neurochemistry, 55: 1031-1041, 1990.

Restriction Official Action Dated Oct. 11, 2012 From the US Patent and Trademark Office Re. U.S. Appl. No. 12/994,761.

Communication Pursuant to Article 94(3) EPC Dated Jun. 25, 2013 From the European Patent Office Re. Application No. 09754337.5.

Official Action Dated Jul. 24, 2013 From the US Patent and Trademark Office Re. U.S. Appl. No. 12/994,761.

International Search Report and the Written Opinion Dated Mar. 14, 2007 From the International Searching Authority Re.: Application No. PCT/IL2006/001410.

International Search Report and the Written Opinion Dated Nov. 23, 2006 From the International Searching Authority Re.: Application No. PCT/IL2006/000699.

International Search Report and the Written Opinion Dated Sep. 30, 2009 From the International Searching Authority Re.: Application No. PCT/IL2009/000525.

Search Report and Written Opinion Dated Sep. 22, 2009 From the Intellectual Property Office of Singapore Issued by the Austrian Patent Office Re.: Application No. 200718734-7.

Translation of Notice of Reason for Rejection Dated Sep. 18, 2009 From the Japanese Patent Office Re.: Application No. 2004-553057.

Bernardo et al. "Optimization of In Vitro Expansion of Human Multipotent Mesenchymal Stromal Cells for Cell-Therapy Approaches: Further Insights in the Search for a Fetal Calf Serum Substitute", Journal of Cellular Physiology, XP002545729, 211(1): 121-130, Apr. 2007.

Capelli et al. "Human Platelet Lysate Allows Expansion and Clinical Grade Production of Mesenchymal Stromal Cells From Small Samples of Bone Marrow Aspirates or Marrow Filter Washouts", Bone Marrow Transplantation, XP002545732, 40(8): 785-791, Oct. 2007.

De Hemptinne et al. "Induction of Glial Glutamate Transporters in Adult Mesenchymal Stem Cells", Journal of Neurochemistry, 91(1): 155-166, Oct. 2004. Abstract, p. 156, Right Col. 'Materials and Methods'—p. 162, Right Col., First §, All Figs.

Doucet et al. "Platelet Lysates Promote Mesenchymal Stem Cell Expansion: A Safety Substitute for Animal Serum in Cell-Based Therapy Applications", Journal of Cellular Physiology, XP002545728, 205(2): 228-236, Nov. 2005.

Farlie et al. "Bcl-2 Transgene Expression Can Protect Neurons Against Developmental and Induced Cell Death", Proc. Natl. Acad. Sci. USA, 92: 4397-4401, May 1995.

Lange et al. "Accelerated and Safe Expansion of Human Mesenchymal Stromal Cells in Animal Serum-Free Medium for Transplantation and Regenerative Medicine", Journal of Cellular Physiology, XP002545733, 213(1): Oct. 18-26, 2007.

Reinisch et al. "Humanized System to Propagate Cord Blood-Derived Multipotent Mesenchymal Stromal Cells for Clinical Application", Regenerative Medicine, XP002545730, 2(4): 371-382, Jul. 2007.

Sadan et al. "Adult Neurotrophic Factor-Secreting Stem Cells: A Potential Nocel Therapy for Neurodegenerative Diseases", The Israeli Medical Association Journal, XP002545735, 11(4): 201-204, Apr. 2009.

Sadan et al. "Migration of Neurotrophic Factors-Secreting Mesenchymal Stem Cells Toward a Quinolinic Acid Lesion as Viewed by Magnetic Resonance Imaging", Stem Cells, XP002545734, 26(10): 2542-2551, Oct. 2008.

Schallmoser et al. "Human Platelet Lysate Can Replace Fetal Bovine Serum for Clinical-Scale Expansions of Functional Mesenchymal Stromal Cells", Transfusion, XP002545731, 47(8): 1436-1446, Aug. 2007.

Wagner et al. "Mesenchymal Stem Cell Preparations—Comparing Apples and Oranges", Stem Cell Reviews, XP002545736, 3(4): 239-248, Dec. 2007.

Communication Pursuant to Rule 58 EPC or Rule 159 EPC, Invitation to Remedy Deficiencies in the Application Document Dated Mar. 29, 2011 From the European Patent Office Re. Application No. 11000994.1.

Communication Pursuant to Article 94(3) EPC Dated Nov. 15, 2013 From the European Patent Office Re. Application No. 11000994.1.

Communication Under Rule 71(3) EPC Dated Dec. 4, 2013 From the European Patent Office Re. Application No. 06766101.7.

Kurozumi et al. "Mesenchymal Stem Cells That Produce Neurotrophic Factors Reduce Ischemic Damage in the Rat Middle Cerebral Artery Occlusion Model", Molecular Therapy, XP004672531, 11(1): 96-104, Jan. 1, 2005.

\* cited by examiner

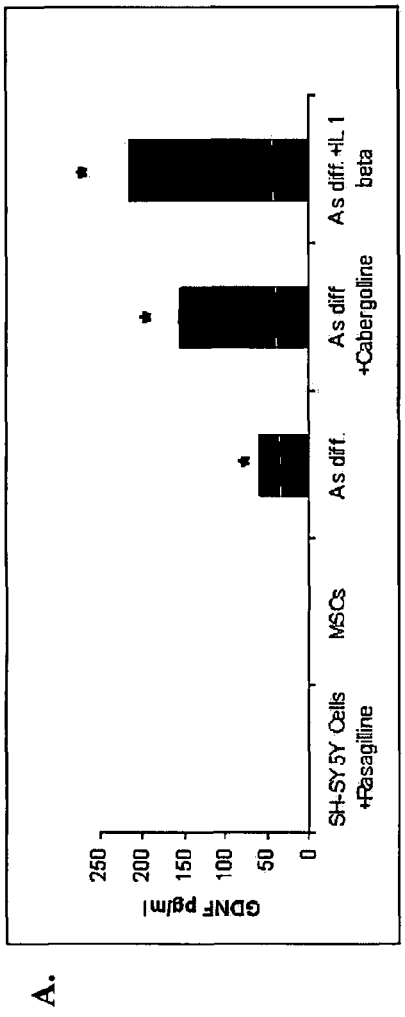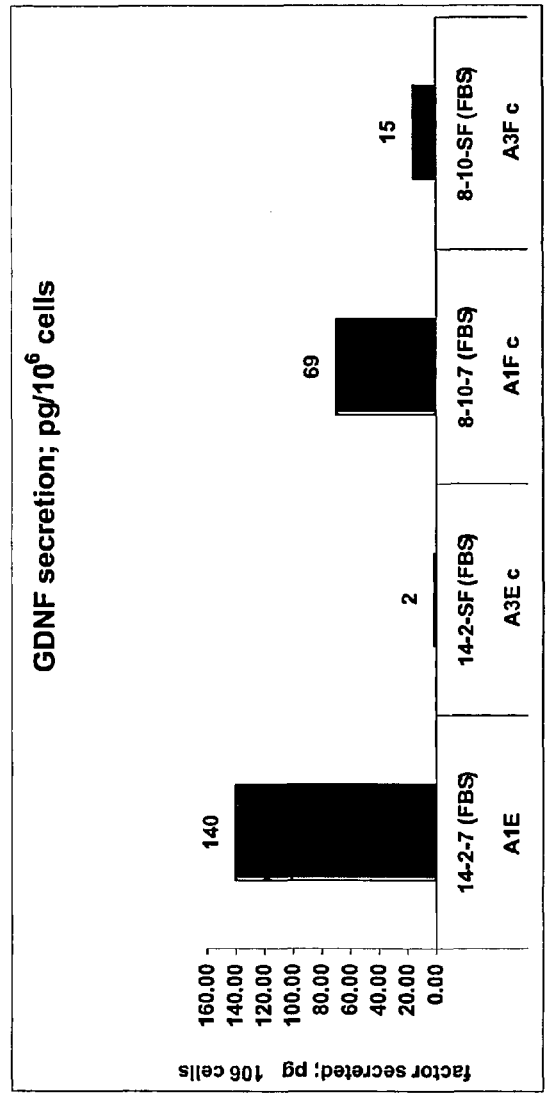
FIGs. 8A-B

FIGs. 14A-E

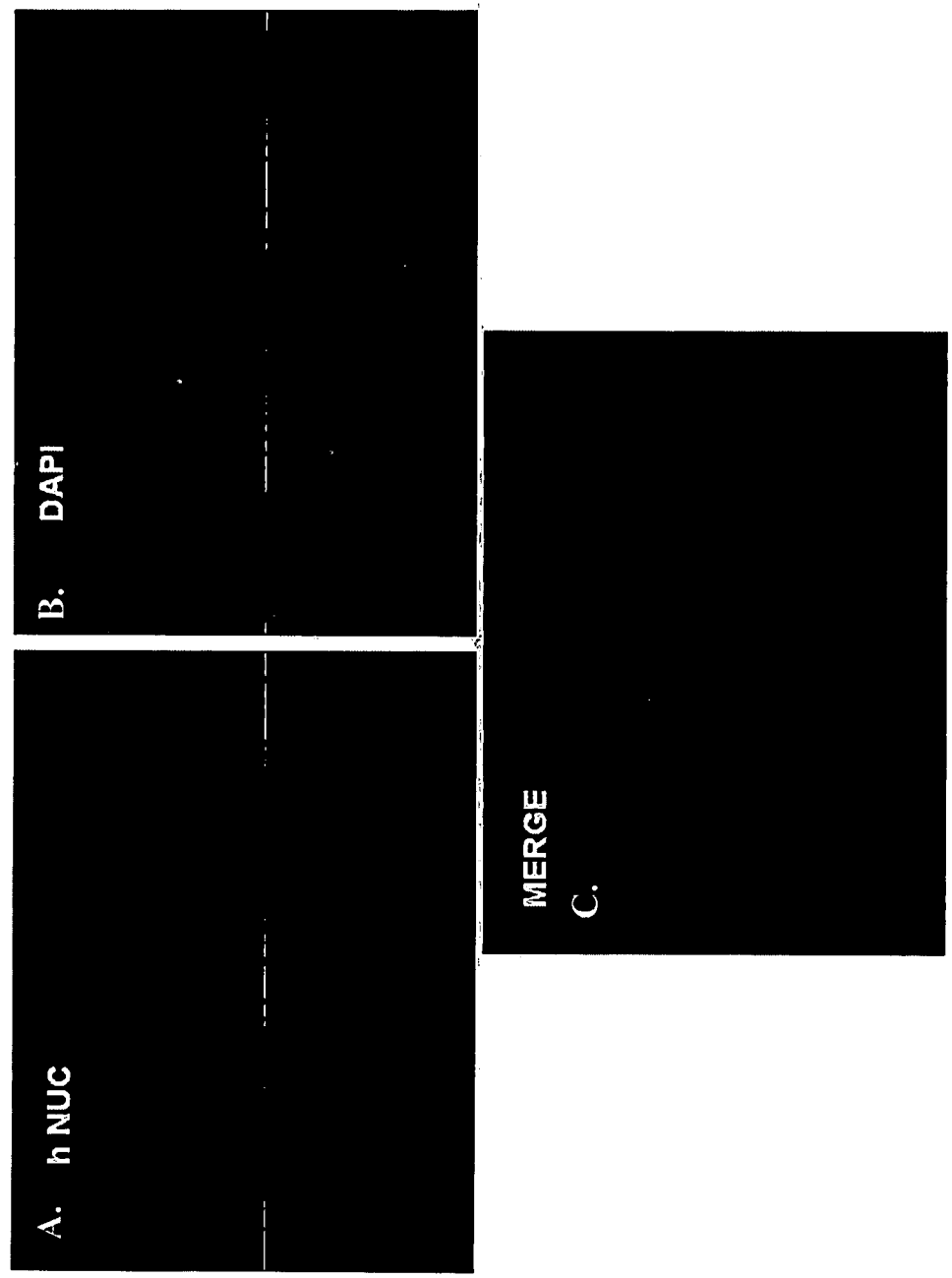
FIG. 17A-C

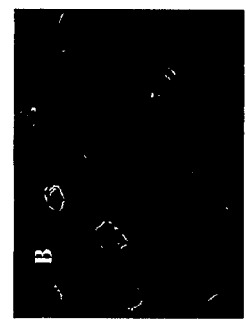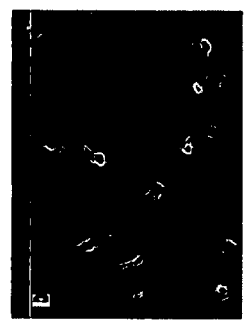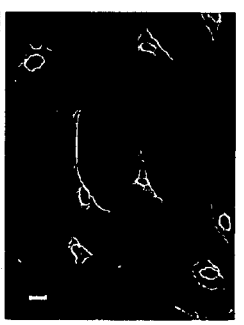
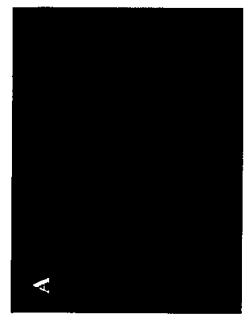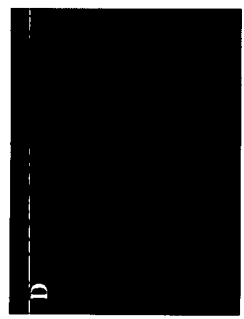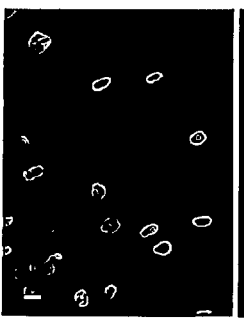
FIGs. 18A-I

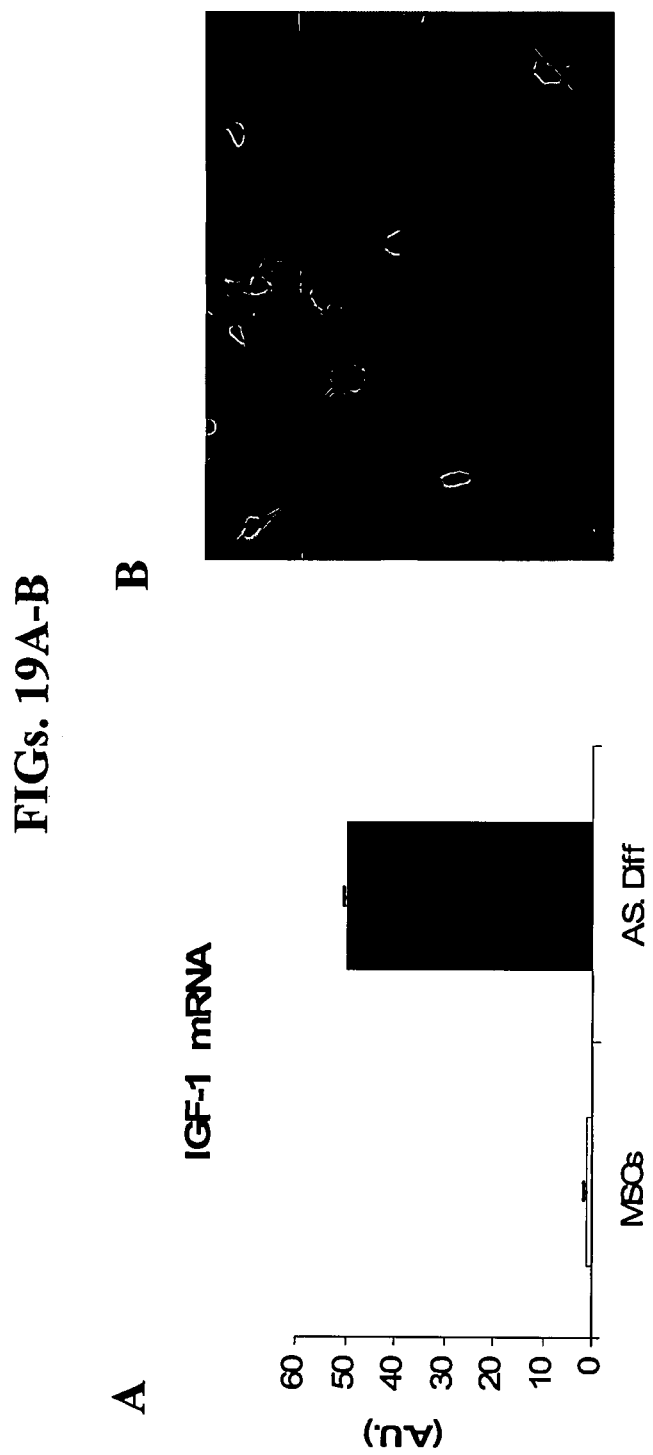
FIGs. 19A-B

FIGs. 20A-C
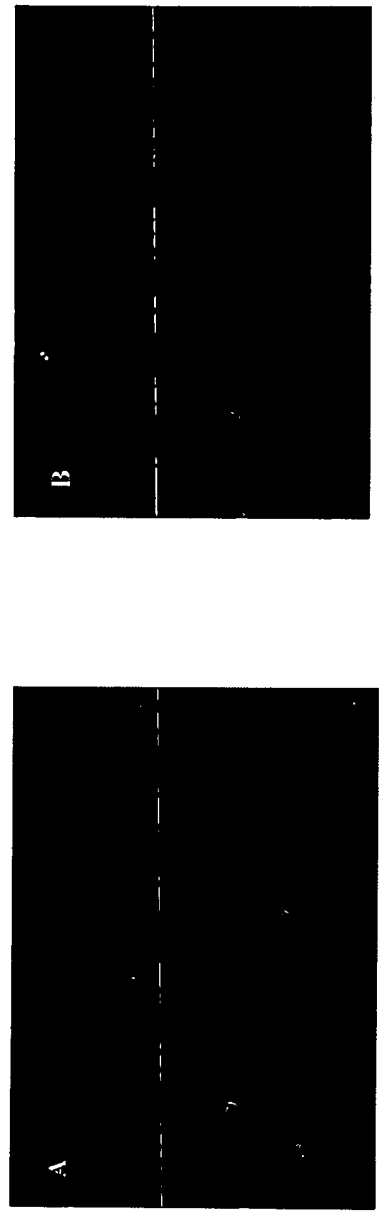
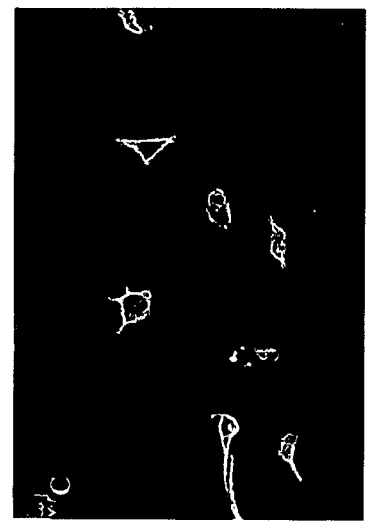

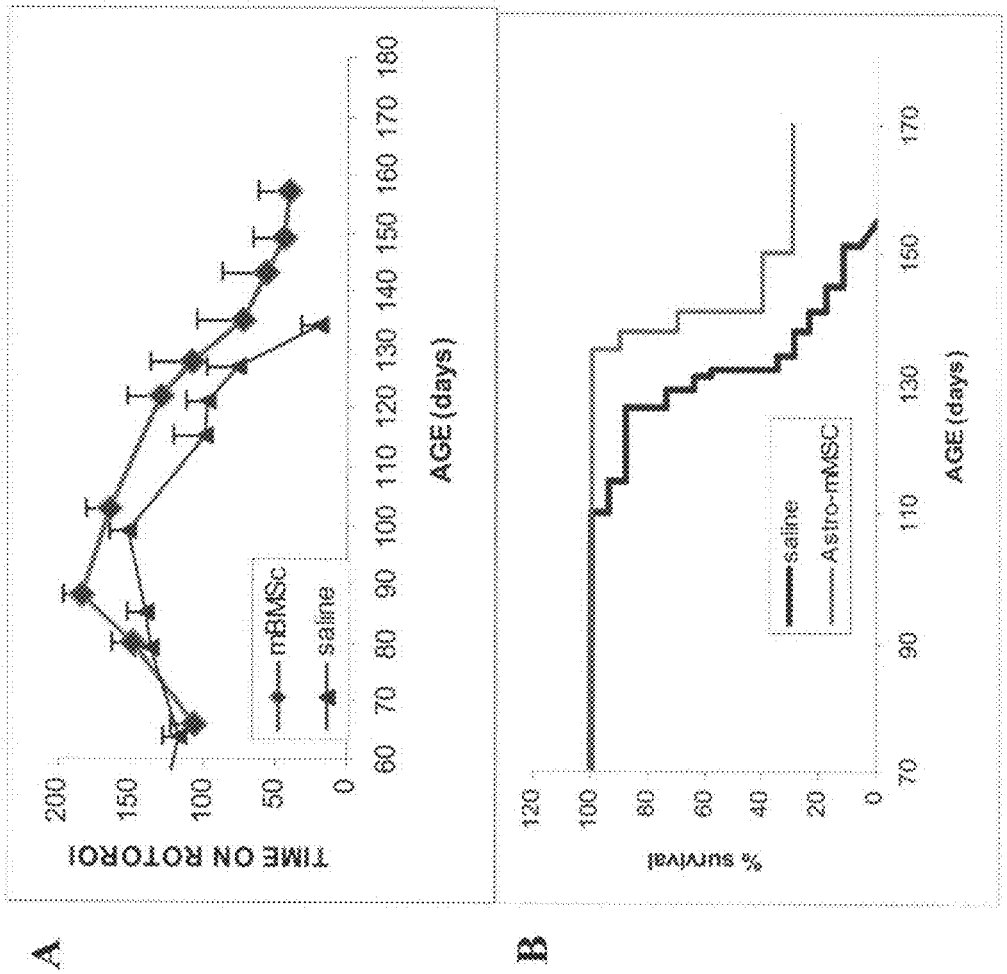
FIGs. 22A-B

ISOLATED CELLS AND POPULATIONS COMPRISING SAME FOR THE TREATMENT OF CNS DISEASES

RELATED APPLICATIONS

This application is a continuation-in-part of PCT Patent Application No. PCT/IL2006/000699, filed on Jun. 18, 2006 which claims the benefit of U.S. Provisional Patent Application No. 60/690,879, filed on Jun. 16, 2005, the contents of which are hereby incorporated by reference.

FIELD AND BACKGROUND OF THE INVENTION

The present invention relates to cells and populations thereof which can be used for treating CNS diseases.

Parkinson's disease is an age-related disorder characterized by progressive loss of dopamine producing neurons in the substantia nigra of the midbrain, which in turn leads to progressive loss of motor functions manifested through symptoms such as tremor, rigidity and ataxia.

Current treatment strategies for PD focus on restoring the depletion of dopamine, generally through the administration of the dopamine precursor L-DOPA (L-3-4-dihydroxyphenylalanine). L-DOPA, (the blood-brain barrier (BBB) penetrating precursor of dopamine), successfully increases the synthesis and release of dopamine. However, as the disease progresses, less dopaminergic neurons are available to synthesize dopamine from the precursor and the effectiveness of the treatment decreases whilst L-DOPA-induced dyskinesia appears. Other treatments with dopamine agonists, monoamine oxidants inhibitor or COMT inhibitors also demonstrate partial improvement but they cannot prevent progression of the disease.

Cell transplantation has been suggested as an alternative treatment option for repairing and replacing missing dopaminergic neurons. For such cell replacement therapy to work, implanted cells must survive and integrate, both functionally and structurally, within the damaged tissue.

The use of stem cells as a cellular source in cell replacement therapy for Parkinson's disease has been recently suggested. Stem cells have the ability to exist in vivo in an undifferentiated state and to self-renew. They are not restricted to cell types specific to the tissue of origin, and so they are able to differentiate in response to local environmental cues from other tissues. This capability of self renewal and differentiation has great therapeutic potential in curing diseases.

In Parkinson's disease the stem cell replacement strategy is based on the idea that restoration of dopamine (DA) neurotransmission is effected by cell grafts that integrate over time into the remaining tissue and produce a long-lasting functional tissue. There are two methods of treating stem cells for grafting in PD. In the first method, prior to transplantation, cells are differentiated in-vitro to dopaminergic neurons. This allows for standardization and quality-control of the relevant cells. The second method comprises transplantation of undifferentiated stem cells that are thought to differentiate in-vivo to dopaminergic neurons following implantation into the striatum or substantia nigra.

In theory, DA neurons for cell therapy in PD could be made from stem cells from four different sources: fetal dopaminergic neurons, neural stem cells, embryonic stem cells and bone marrow stem cells.

Bone marrow contains two major populations of stem cells: hematopoietic stem cells (HSCs) and mesenchymal stem cells (MSCs) occasionally referred to as bone marrow stromal cells.

Rat BMSC following differentiation were shown to express Tyrosine-hydroxylase (TH), choline acetyltransferase and beta-III tubulin [Woodbury, D., et al., J Neurosci Res. 69(6):908-17, 2002]. Clinical therapeutic potential of mouse BMSC in PD was demonstrated by injecting mouse BMSC intrastriatally to 1-methyl-4-phenyl-1,2,3,6-tetrahydropyridine (MPTP) mouse model of PD. The transplanted cells survived and expressed TH. Moreover improvement on the rotorod test at 35 days following transplantation was indicated [Li, Y., et al., Neurosci Lett. 316(2):67-70, 2001].

U.S. Patent Appl. 20050265983 to the present inventors teach human dopamine synthesizing MSCs which expressed neuronal markers and transcription factors that characterize midbrain DA neuron following induction of neuronal differentiation.

As an alternative to a cell replacement strategy, where the grafted cells have to survive and possess morphological electrophysiological and functional dopaminergic properties, cell therapy may be aimed at restoring or reestablishing the normal anatomy (connectivity) and physiology (appropriate synaptic contacts and functioning) of the striatum.

Neurotrophic factors (NTFs) are secreted proteins that regulate the survival, functional maintenance and phenotypic development of neuronal cells. Alterations in NTF levels are involved in triggering programmed cell-death in neurons and thus contribute to the pathogenesis of Parkinson's and other neurodegenerative diseases.

One of the most potent NTF for dopaminergic neurons is called glial cell line-derived neurotrophic factor (GDNF). It is known to promote the survival of the dopaminergic neurons in the substantia nigra, promote neurite outgrowth, increase cell body size and also raise levels of TH. GDNF belongs to a family of proteins, related to the TGF-β-superfamily, currently consisting of four neurotrophic factors: GDNF, Neurturin (NTN), Persephin, and Artemin/Neublastin. These factors are known to serve as regulators of cell proliferation and differentiation.

An analysis of neural progenitor cells (ST14A) revealed that GDNF overproduction may be associated with up-regulation of genes involved in axonal sprouting, neurite outgrowth, spine formation, vesicle transport and synaptic plasticity [Pahnke J, et al, Exp Cell Res. 297(2):484-94, 2004]. It was also suggested that the neuroprotective activity of GDNF is via its activation of the antioxidant enzyme systems such as glutathione peroxidase, superoxide dismutase and catalase activities [Chao C C, Lee E H. Neuropharmacology, 38(6): 913-6, 1999].

Various cells type produce GDNF including glia cells (oligodendrocytes and astrocyte), neuroblastoma and glioblastoma cell lines. It has recently been shown that rat BMSCs cultured in DMEM supplemented with 20% fetal bovine serum, at passage 6 express GDNF and NGF [Garcia R, et al., Biochem Biophys Res Commun. 316(3):753-4, 2004].

GDNF synthesis can be regulated by growth factors, hormones, cytokines and neurotransmitters. For example, tumor necrosis factor-α or interleukin-1 induces release of GDNF from glioblastoma cells. Forskolin or cAMP causes an increase in GDNF release by both the neuroblastoma and glioblastoma cell lines. These cells comprise neurotransmitter receptors, which allow the neurotransmitters to regulate growth factor production under conditions of stress.

Administration of GDNF directly into the brain has been shown to be effective in various animal models of PD. In addition, exposure of cells to GDNF prior to transplant has proven beneficial. For instance, grafting of 400,000 fetal dopaminergic neurons prior to transplantation significantly improved the rotational behavior of lesioned rats [Mehta V, et al., J. Neurosurg. 1999 April; 90(4):804-6].

Various methods have been used to aid administration of GDNF into the brain including osmotic pumps, capsules and microspheres. Another approach for GDNF delivery is in vivo gene therapy. Bone marrow mesenchymal cells genetically engineered to express GDNF, transplanted into MPTP-lesioned mice, were able to protect nigral neurons as well as striatal fibers [Park, K., Neurosci. Res. 40: 315-323, 2001].

Several studies have shown that MSCs following exposure to different factors in vitro, change their phenotype and demonstrate neuronal and glial markers [Kopen, G. C., et al., Proc Natl Acad USA. 96(19):10711-6, 1999; Sanchez-Ramos, et al. Exp Neurol. 164(2):247-56. 2000; Woodbury, D., J Neurosci Res. 61(4):364-70, 2000; Woodbury, D., et al., J Neurosci Res. 69(6):908-17, 2002; Black, I. B., Woodbury, D. Blood Cells Mol Dis. 27(3):632-6, 2001; Kohyama, J., et al. Differentiation. 68(4-5):235-44, 2001; Levy, Y. S. J Mol Neurosci. 21(2):121-32, 2003].

However, none of these studies have shown human MSCs capable of secreting significant levels of neurotrophic factors.

There is thus a widely recognized need for, and it would be highly advantageous to have, transplantable cells capable of synthesizing neurotrophic factors such as GDNF for the treatment of neurodegenerative disorders.

SUMMARY OF THE INVENTION

According to the present invention there is provided an isolated human cell comprising at least one astrocytic phenotype and at least one mesenchymal stem cell phenotype, wherein the mesenchymal stem cell phenotype is not an astrocytic phenotype.

According to another aspect of the present invention there is provided an isolated human cell comprising at least one mesenchymal stem cell phenotype and at least one astrocytic structural phenotype, wherein the mesenchymal stem cell phenotype is not an astrocytic structural phenotype.

According to yet another aspect of the present invention there is provided an isolated human cell comprising at least one mesenchymal stem cell phenotype and at least one astrocytic functional phenotype, wherein the mesenchymal stem cell phenotype is not an astrocytic functional phenotype.

According to still another aspect of the present invention there is provided an isolated human cell comprising at least one mesenchymal stem cell phenotype and expressing at least one neurotrophic factor, wherein the expression is at least 2 times greater than a basal expression of the neurotrophic factor in a mesenchymal stem cell.

According to an additional aspect of the present invention there is provided an isolated cell population comprising human cells wherein:
(i) at least N % of the human cells comprise at least one astrocytic phenotype;
(ii) at least M % of the human cells comprise at least one mesenchymal stem cell phenotype, the mesenchymal stem cell phenotype is not an astrocytic phenotype; and (iii) at least one of the human cells comprises both the at least one astrocytic phenotype and the at least one mesenchymal stem cell phenotype;
where M and N are each independently selected between 1 and 99.

According to yet an additional aspect of the present invention there is provided an isolated cell population comprising human cells wherein:
(i) at least N % of the human cells express at least one neurotrophic factor, wherein the expression is at least 2 times greater than a basal expression of the neurotrophic factor in a mesenchymal stem cell;
(ii) at least M % of the human cells comprise at least one mesenchymal stem cell phenotype; and
(iii) at least one of the human cells expresses the at least one neurotrophic factor and the at least one mesenchymal stem cell phenotype;
where M and N are each independently selected between 1 and 99.

According to still an additional aspect of the present invention there is provided an isolated cell population comprising human cells wherein:
(i) at least N % of the human cells comprise at least one astrocytic structural phenotype;
(ii) at least M % of the human cells comprise at least one mesenchymal stem cell phenotype, the mesenchymal stem cell phenotype is not an astrocytic structural phenotype; and
(iii) at least one of the human cells comprise both the at least one astrocytic structural phenotype and the at least one mesenchymal stem cell phenotype;
where M and N are each independently selected between 1 and 99.

According to a further aspect of the present invention there is provided an isolated cell population comprising human cells wherein:
(i) at least N % of the human cells comprise at least one astrocytic functional phenotype;
(ii) at least M % of the human cells comprise at least one mesenchymal stem cell phenotype, the mesenchymal stem cell phenotype is not an astrocytic functional phenotype; and
(iii) at least one of the human cells comprise both the at least one astrocytic functional phenotype and the at least one mesenchymal stem cell phenotype;
where M and N are each independently selected between 1 and 99.

According to yet a further aspect of the present invention there is provided a method of generating astrocyte-like cells, comprising incubating mesenchymal stem cells in a differentiating medium comprising platelet derived growth factor (PDGF) and human neuregulin 1-β1, thereby generating astrocyte-like cells.

According to still a further aspect of the present invention there is provided a method of generating astrocyte-like cells, comprising incubating mesenchymal stem cells in a medium comprising at least one differentiating agent, the at least one differentiating agent being selected from the group consisting of platelet derived growth factor (PDGF), human neuregulin 1-β1, FGF2, EGF, N2, IBMX and cAMP, thereby generating astrocyte-like cells.

According to still a further aspect of the present invention there is provided a method of treating a CNS disease or disorder comprising administering to an individual in need thereof a therapeutically effective amount of astrocyte-like cells, thereby treating the CNS disease or disorder.

According to still a further aspect of the present invention there is provided a use of astrocyte-like cells for the treatment of a CNS disease or disorder.

According to still a further aspect of the present invention there is provided a pharmaceutical composition comprising as an active agent any of the cells or cell populations of any of claims 1, 2, 3, 4, 5, 6, 7 or 8 and a pharmaceutically acceptable carrier.

According to further features in preferred embodiments of the invention described below, the cells are non-genetically manipulated.

According to still further features in the described preferred embodiments, the at least one astrocytic phenotype is a structural phenotype.

According to still further features in the described preferred embodiments, the at least one astrocytic phenotype is a functional phenotype.

According to still further features in the described preferred embodiments, the cells further comprise an astrocytic functional phenotype.

According to still further features in the described preferred embodiments, the astrocytic functional phenotype is not the mesenchymal stem cell phenotype.

According to still further features in the described preferred embodiments, the cells further comprise an astrocytic structural phenotype.

According to still further features in the described preferred embodiments, the cells further comprise an astrocytic structural phenotype.

According to still further features in the described preferred embodiments, the astrocytic structural phenotype is not the mesenchymal stem cell phenotype.

According to still further features in the described preferred embodiments, the astrocytic structural phenotype is a cell size, a cell shape, an organelle size and an organelle number.

According to still further features in the described preferred embodiments, the astrocytic structural phenotype is expression of at least one astrocytic marker.

According to still further features in the described preferred embodiments, the astrocytic marker is a surface marker.

According to still further features in the described preferred embodiments, the astrocytic marker is an internal marker.

According to still further features in the described preferred embodiments, the astrocytic functional phenotype is expression of at least one neurotrophic factor at a level at least 2 times greater than a basal production of the neurotrophic factor in a mesenchymal stem cell.

According to still further features in the described preferred embodiments, the at least one neurotrophic factor is selected from the group consisting of glial derived neurotrophic factor (GDNF), nerve growth factor (NGF), brain-derived neurotrophic factor (BDNF), neurotrophin-3 (NT-3), neurotrophin-4/5, Neurturin (NTN), Persephin, brain derived neurotrophic factor (BDNF), artemin (ART), ciliary neurotrophic factor (CNTF), insulin growth factor-I (IGF-1) and Neublastin.

According to still further features in the described preferred embodiments, the at least one neurotrophic factor is GDNF.

According to still further features in the described preferred embodiments, the astrocyte marker is selected from the group consisting of S100 beta, glial fibrillary acidic protein (GFAP), glutamine synthetase, GLT-1 and GLAST.

According to still further features in the described preferred embodiments, the secretion of the GDNF is regulated by IL-1 beta and/or cabergoline.

According to still further features in the described preferred embodiments, a duration of the incubating is about 48 hours.

According to still further features in the described preferred embodiments, a concentration of the PDGF is about 5 ng/ml.

According to still further features in the described preferred embodiments, a concentration of the human neuregulin 1-β1 is about 50 ng/ml.

According to still further features in the described preferred embodiments, the differentiating medium further comprises L-glutamine, dibutyryl cyclic AMP and isobutylmethylxanthine IBMX.

According to still further features in the described preferred embodiments, the method further comprises culturing the cells in an additional medium prior to the incubating thereby predisposing the cells to differentiate into astrocyte-like cells.

According to still further features in the described preferred embodiments, the additional medium comprises human epidermal growth factor (hEGF) and human basic fibroblast growth factor (hbFGF).

According to still further features in the described preferred embodiments, a concentration of hEGF is about 20 ng/ml.

According to still further features in the described preferred embodiments, a concentration of hbFGF is about 20 ng/ml.

According to still further features in the described preferred embodiments, the additional medium further comprises L-glutamine, insulin, progesterone, putrescin, selenium and transferrin.

According to still further features in the described preferred embodiments, a duration of the culturing is about 48 hours.

According to still further features in the described preferred embodiments, the mesenchymal stem cells are obtained by: (a) culturing a population of cells comprising the mesenchymal stem cells in a proliferating medium capable of maintaining and/or expanding the mesenchymal stem cells; and (b) selecting mesenchymal stem cells from the cells resulting from step (a).

According to still further features in the described preferred embodiments, the step (b) is affected by harvesting surface adhering cells.

According to still further features in the described preferred embodiments, the method further comprises administering to the individual, stem cells capable of endogenously synthesizing at least one neurotransmitter.

According to still further features in the described preferred embodiments, the CNS disease or disorder is a neurodegenerative disease or disorder.

According to still further features in the described preferred embodiments, the CNS disease or disorder is selected from the group consisting of a motion disorder, a dissociative disorder, a mood disorder, an affective disorder, an addictive disorder and a convulsive disorder.

According to still further features in the described preferred embodiments, the neurodegenerative disorder is selected from the group consisting of Parkinson's, multiple sclerosis, epilepsy, amyotrophic lateral sclerosis, stroke, autoimmune encephalomyelitis, diabetic neuropathy, glaucomatous neuropathy, Alzheimer's disease and Huntingdon's disease.

According to still further features in the described preferred embodiments, the cells are autologous cells.

According to still further features in the described preferred embodiments, the cells are non-autologous cells.

The present invention successfully addresses the shortcomings of the presently known configurations by providing cells and populations thereof capable of secreting neurotrophic factors.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4B is a bar graph illustrating the level of GFAP in cell extracts of the differentiated human MSCs as analyzed by real time PCR using primers SEQ ID NOs: 11 and 12.

FIG. 6B illustrates that the number of the cells that positively stained with anti-GDNF was about 30% (*P<0.05, n=3, average cells counted per n=415.5±37.5). The number of GDNF cells was evaluated by examination of 15 fields from three independent cultures. The total number of cells in these samples was determined by counting DAPI stained cell nuclei and results are expressed as mean±SEM percentages of positive cells.

FIGS. 8A-D are bar graphs illustrating the quantity of GDNF, BDNF and NGF secreted by the differentiated human MSCs. FIG. 8A illustrates the effect of a 48 hour incubation of cabergoline (130 pg/ml) and IL-1β (100 pg/ml) on the secretion of GDNF. Culture media was collected following 72 h of differentiation and analyzed using ELISA. Results are the mean±S.D. of three independent experiments. Differences where p<0.05 (*) were significant when compared with controls. Differentiated cell media was also assayed for GDNF (FIG. 8B) and NGF (FIG. 8C). (Donor #14-2, #8-10 or # H1-2-7. The blue bars depict secretion following differentiation and the red bars depict secretion prior to differentiation. FIG. 8D illustrates the effect of a 48 hour differentiation on BDNF secretion in MSCs from three different donors.

FIG. 14A illustrates DAPI staining. FIG. 14B illustrates human nuclear antigen staining. FIG. 14C illustrates GFAP staining. FIG. 14D is a merge of all three stainings. Immunostaining and confocal microscopy study revealed that up to 25% of the cells that were positive for human antigen were also positive for GFAP.

FIGS. 17A-C are confocal microscopy images on cells of ALS mice transplanted with astrocyte differentiated hBMSc illustrating that the astrocyte differentiated BMSC transplanted into the gastrocnemius of ALS mice survive 110 days post transplantation.

FIGS. 18A-I are confocal microscopy images illustrating the expression of neurotrophic factors in astrocyte-differentiated hBMSC (AS. Diff.) and hBMSC grown in serum free (S.F.) media. The astrocyte satellite-like morphology and positive staining for GDNF is demonstrated in the differentiated BMSC (FIGS. 18B and 18C) compared to BMSC grown in S.F. medium (FIG. 18A). Staining for NGF, BDNF, and CNTF in represented in AS. Diff. cells (FIGS. 18E, 18G and 18I) and is absent in SF. BMSCs (FIGS. 18D, 18F and 18H). The specific primary antibodies were visualized with secondary antibodies conjugated with Alexa fluorescents 488 (green) or 568 (red). Nuclear DNA was stained with DAPI (blue). Photographs were taken at ×200 magnification or ×400 (FIG. 18C).

FIGS. 19A-B illustrate that astrocyte differentiated BMSCs express IGF-1 transcript. FIG. 19A is a bar graph illustrating real time PCR of IGF-1 mRNA in astrocyte-differentiated BMSC (As. Diff.) and BMSC grown in serum free media. FIG. 19B is a confocal microscopy image illustrating immunostaining for IGF-1 receptor represented in astrocyte differentiated cells. Y-axis values represent ratio of the specific mRNAs normalized to GAPDH in means±SEM for three experiments. P<0.05, compared to serum free treated MSC. Alexa fluorescents 488 (green) and nuclear stained with DAPI (blue). Photographs were taken at ×200 magnification.

FIGS. 20A-C are confocal microscopy images illustrating that GFAP is co-expressed with GDNF in the astrocyte differentiated BMSCs of the present invention. AS. Diff. were stained with antibodies against the GDNF (green) and GFAP (red) (FIGS. 20A and 20B respectively). Colocalization of the astrocyte marker as well as GDNF is represented in FIG. 20C. Photographs were taken at ×200.

FIGS. 22A-B are graphs illustrating the improved symptoms (FIG. 22A) and survival (FIG. 22B) of SOD1 Tg mice (a mouse model of ALS) following transplantation of the astrocyte differentiated cells of the present invention as compared to the saline control mice.

DESCRIPTION OF THE PREFERRED EMBODIMENTS

The present invention relates to cells and populations thereof which can be transplanted into a patient in order to treat a myriad of neurodegenerative diseases.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Neurotrophic factors (NTFs) are secreted proteins that regulate the survival, functional maintenance and phenotypic development of neuronal cells. Alterations in NTF levels are involved in triggering programmed cell-death in neurons and thus contribute to the pathogenesis of Parkinson's and other neurodegenerative diseases.

One of the most potent NTF for dopaminergic neurons is called glial cell line-derived neurotrophic factor (GDNF). It is known to promote the survival of the dopaminergic neurons in the substantia nigra, promote neurite outgrowth, increase cell body size and also raise levels of TH.

However, direct use of neurotrophic factors in general, and GDNF in particular, is prohibited as they do not pass the blood-brain barrier and do not distribute properly following systemic injection. Therefore, other strategies must be developed in order to take advantage of their therapeutic properties.

Whilst reducing the present invention to practice, the present inventors have found that under specific culturing conditions mesenchymal stem cells (MSCs) may be differentiated into cells having an astrocytic phenotype capable of secreting neurotrophic factors. This outcome was shown to be both donor and passage-independent. Accordingly, the present inventors have shown that such differentiated MSCs can be used to treat patients with neurodegenerative diseases following transplantation.

Figure 7:
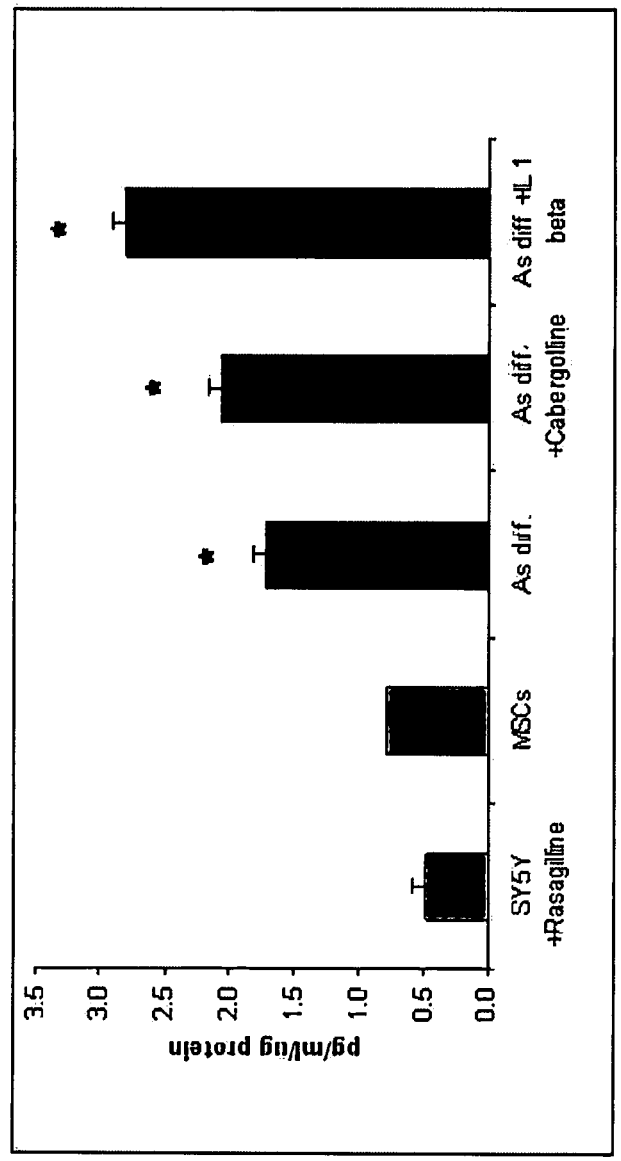
FIG. 7 is a bar graph illustrating the quantity of GDNF present in the cell in the differentiated human MSC. Production of GDNF was assayed in cell extracts of the differentiated hBMSc by ELISA. Results are the mean±S.D. of three independent experiments. Differences where p<0.05 (*) were significant when compared with controls. Differentiated cells were incubated with cabergoline (130 pg/ml) and IL-1β (100 pg/ml) 24 hours following initiation of differentiation for 48 hours.
Figure 8C:
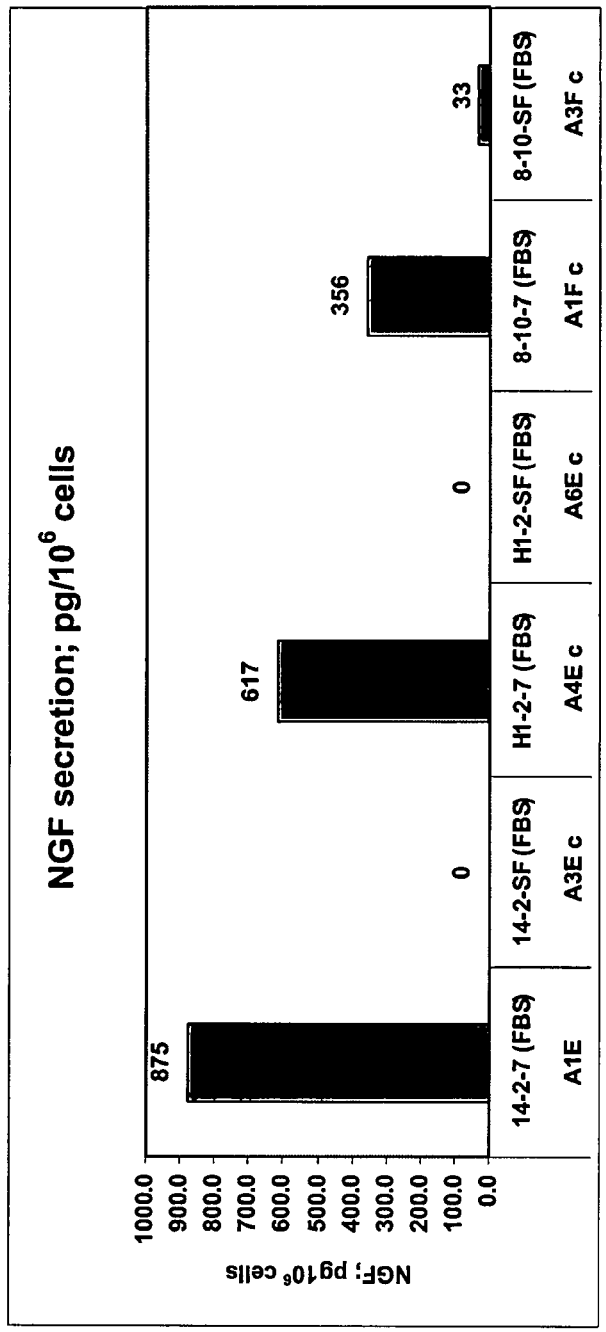
Figure 8D:
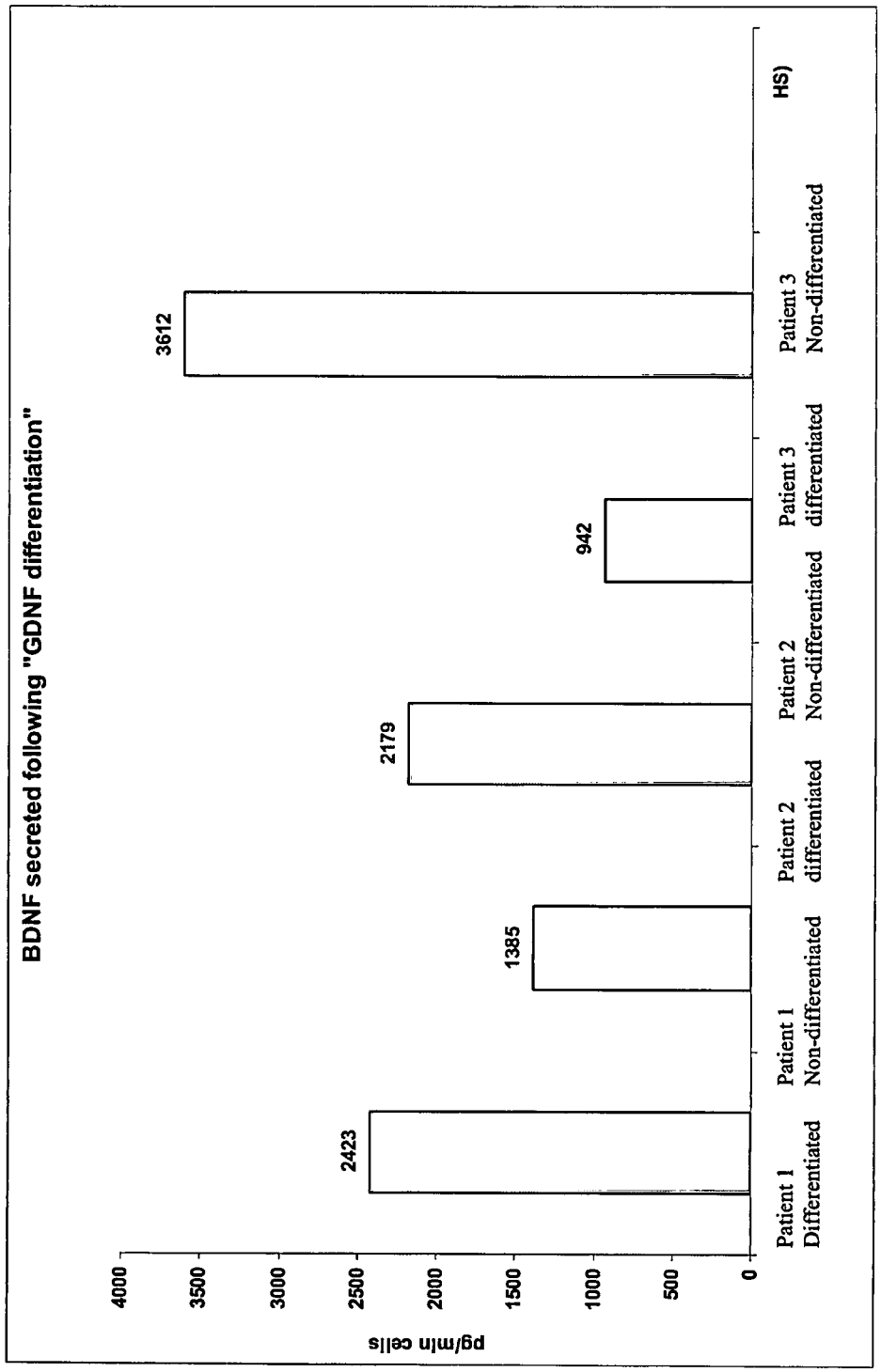
Figure 10:
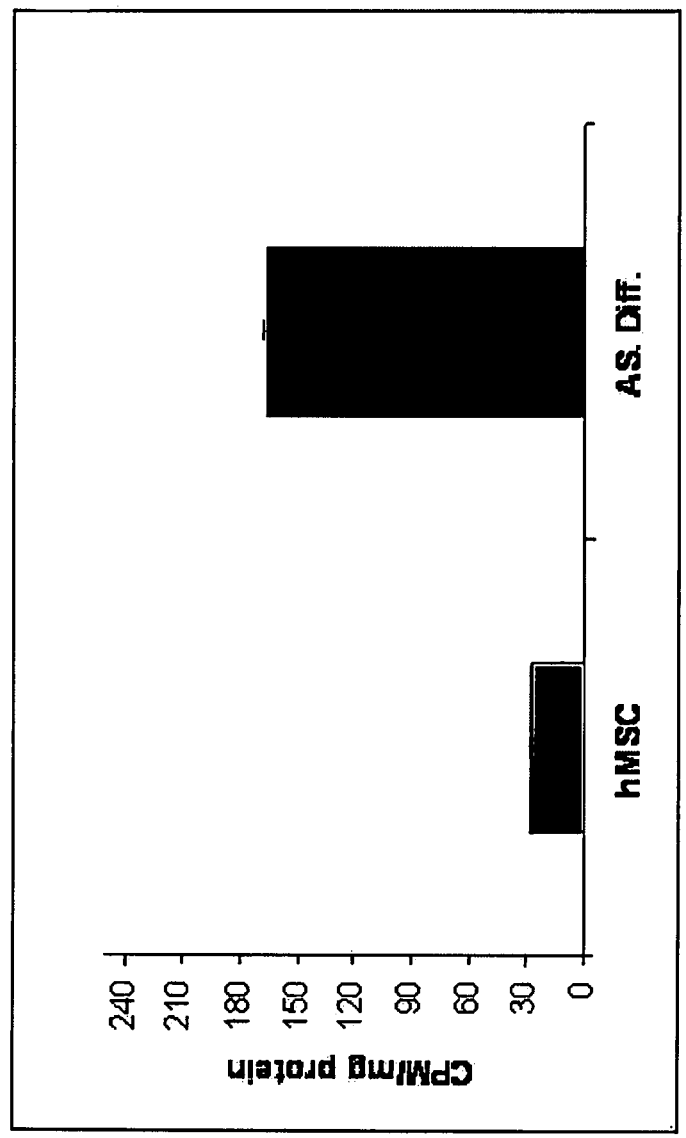
FIG. 10 is a bar graph illustrating the functional activity of glutamate transporters prior to and following astocyte differentiation of hBMSCs. The [$^3$H]d-aspartate uptake (20 nm) was measured in hBMSCs grown in differentiation medium compared to cells grown in serum free medium. Data shown are mean±SEM from triplicate measures performed on three independent cultures. Statistical analysis was performed by one-way anova followed by the Newman-Keul's test for multiple comparisons (p<0.05).

The present inventors have shown that MSCs differentiated according to a novel two-step protocol represent an astrocyte like shape (FIGS. 1A-B and 2A-D) accompanied by the presence of astrocyte markers (FIGS. 3A-B and 4A-B). These astrocyte-like cells were shown to express (FIG. 5, FIGS. 18A-I, FIGS. 19A-B and FIGS. 20A-C) and secrete (FIGS. 8A-D) significant levels of GDNF, BDNF and NGF. Moreover the NTF production was further up-regulated by cabergoline, a D2-receptor agonist and IL-1 (FIG. 7 and FIG. 8A). In addition, the astrocyte-like cells possessed glutamate-clearance machinery (FIG. 10).

Following transplantation into the striatum of 6-OHDA lesioned rat or mouse (a rodent model for Parkinson's) and into the foot muscles of ALS transgenic mice, the cells survived and improved behavioral deficits examined by a rotor rod test, and apomorphine induced rotational behavior (FIGS. 11-17A-C and FIGS. 21-22A-B).

Thus, according to one aspect of the present invention there is provided a method of generating astrocyte-like cells, comprising incubating mesenchymal stem cells in a differentiating medium comprising platelet derived growth factor (PDGF) and human neuregulin 1-β1, thereby generating astrocyte-like cells.

As used herein the phrase "astrocyte-like cells" refers to cells comprising at least one astrocytic phenotype which allows same to in vivo mediate an astrocytic activity, i.e., support of neurons.

Such phenotypes are further described hereinbelow.

The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage. The mesenchymal stem cells of the present invention may be of a syngeneic or allogeneic source, although the first is preferred.

According to a preferred embodiment of this aspect of the present invention the mesenchymal stem cells are not genetically manipulated (i.e. transformed with an expression construct) to generate the cells and cell populations described herein.

It will be appreciated that the cells of the present invention may be derived from any stem cell, although preferably not ES cells.

Mesenchymal stem cells may be isolated from various tissues including but not limited to bone marrow, peripheral blood, blood, placenta and adipose tissue. A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301].

According to a preferred embodiment of this aspect of the present invention, the mesenchymal stem cells are human.

Bone marrow can be isolated from the iliac crest of an individual by aspiration. Low-density BM mononuclear cells (BMMNC) may be separated by a FICOL-PAGUE density gradient. In order to obtain mesenchymal stem cells, a cell population comprising the mesenchymal stem cells (e.g. BMMNC) may be cultured in a proliferating medium capable of maintaining and/or expanding the cells. According to one embodiment the populations are plated on polystyrene plastic surfaces (e.g. in a flask) and mesenchymal stem cells are isolated by removing non-adherent cells. Alternatively mesenchymal stem cell may be isolated by FACS using mesenchymal stem cell markers (see Table 1, hereinbelow).

Preferably the MSCs are at least 50% purified, more preferably at least 75% purified and even more preferably at least 90% purified.

Following isolation the cells are typically expanded by culturing in a proliferation medium capable of maintaining and/or expanding the isolated cells ex vivo as described in Example 1 hereinbelow. The proliferation medium may be DMEM, alpha-MEM or DMEM/F12. Preferably, the proliferation medium is DMEM. Preferably, the proliferation medium further comprises SPN, L-glutamine and a serum (such as fetal calf serum or horse serum) such as described in Example 1 of the Examples section which follows.

Differentiation to astrocyte-like cells can be effected by incubating the MSCs in differentiating media such as those described in U.S. Pat. No. 6,528,245 and by Sanchez-Ramos et al. (2000); Woodburry et al. (2000); Woodburry et al. (J. Neurisci. Res. 96:908-917, 2001); Black and Woodbury (Blood Cells Mol. Dis. 27:632-635, 2001); Deng et al. (2001), Kohyama et al. (2001), Reyes and Verfatile (Ann. N.Y. Acad. Sci. 938:231-235, 2001) and Jiang et al. (Nature 418:47-49, 2002).

BMSc are preferably incubated in an "additional medium" for at least 24 hours, preferably 48 hours, prior to their incubation in a "differentiation medium". Incubation in "differentiation medium" extends for at least 24 hours, preferably at least 48 hours.

The differentiating media (including the additional differentiating medium) may be DMEM or DMEM/F12, preferably DMEM. A suitable "additional medium" may be any growth medium capable of predisposing the cells to astrocyte-like differentiation, such as a growth medium supplemented with epidermal growth factor hEGF (e.g. 20 ng/ml) and/or basic fibroblast growth factor (e.g. 20 ng/ml). Preferably, the additional medium also comprises N2 supplement (insulin, progesterone, putrescin, selenium and transferrin)

The differentiating medium of the present invention preferably comprises platelet derived growth factor (e.g. 5 ng/ml) and human neuregulin 1-β1 (e.g. 50 ng/ml). The "differentiating medium" preferably includes differentiating agents such as IL-1β and/or dbcAMP.

Preferably the differentiating media further comprise SPN, L-glutamine, a supplement (such as N2 or B27), antibiotic (e.g. IBMX) and a serum (such as fetal calf serum, fetal bovine serum or horse serum).

According to another aspect of the present invention, the mesenchymal stem cells are incubated in a medium comprising at least one differentiating agent in order to generate the astrocyte-like cells of the present invention. Examples of differentiating agents include, but are not limited to platelet derived growth factor (PDGF), human neuregulin 1-β1, FGF2, EGF, N2 supplement, IBMX and cAMP.

The differentiating media (including the additional differentiating medium) may also comprise other agents such as neurotrophic factors (e.g. BDNF, CNTF, GDNF, NTN, NT3 or LIF), hormones, growth factors (e.g. GGF2, TGF-β3, TGF-α, FGF-8 and bFGF), vitamins, hormones e.g., insulin, progesterone and other factors such as sonic hedgehog, bone morphogenetic proteins, forskolin, retinoic acid, ascorbic acid, putrescin, selenium and transferrin.

Exemplary differentiating media are described in Example 1 hereinbelow.

Cell populations obtained according to the methods describe herein are typically non-homogeneous.

Thus, according to another aspect of the present invention there is provided an isolated population of human cells wherein:

(i) at least N % of the cells comprise at least one astrocytic phenotype;

(ii) at least M % of the cells comprise at least one mesenchymal stem cell phenotype, the mesenchymal stem cell phenotype is not an astrocytic phenotype; and (iii) at least one of the human cells comprises both the at least one astrocytic phenotype and the at least one mesenchymal stem cell phenotype; where M and N are each independently selected between 1 and 99.

The term "isolated" as used herein refers to a population of cells that has been removed from its in-vivo location (e.g. bone marrow, neural tissue). Preferably the isolated cell population is substantially free from other substances (e.g., other cells) that are present in its in-vivo location.

As used herein, the phrase "astrocytic phenotype" refers to a structural and/or functional parameter typical (e.g. unique) to an astrocyte which may be used to distinguish between the differentiated MSCs of the present invention and non-differentiated MSCs. The astrocytic phenotype may comprise a single or a number of features which may be used to distinguish between the differentiated MSCs of the present invention and non-differentiated MSCs.

It will be appreciated that the functional parameters may overlap with the structural parameter e.g., presence of secretory vesicles.

Preferably the functional astrocytic phenotype comprises the ability to express a neurotrophic factor at a level at least 2 times greater than a basal expression of the neurotrophic factor in a non-differentiated human mesenchymal stem cell.

As used herein the term "express" refers to the synthesis and/or secretion of the above-mentioned neurotrophic factor. Since the neurotrophic factor elicits its effects outside the cell, preferably the secretion of the neurotrophic factor is increased in the cells of the populations of the present invention. According to a preferred embodiment the secretion is increased at least 2 fold compared to the amount of neurotrophic factor that is secreted in non-differentiated human mesenchymal stem cells and even more preferably 5 fold.

As used herein, the phrase "neurotrophic factor" refers to a cell factor that acts on the cerebral nervous system comprising growth, differentiation, functional maintenance and/or survival effects on neurons. Examples of neurotrophic factors include, but are not limited to, glial derived neurotrophic factor (GDNF), GenBank accession nos. L19063, L15306; nerve growth factor (NGF), GenBank accession no. CAA37703; brain-derived neurotrophic factor (BDNF), GenBank accession no CAA62632; neurotrophin-3 (NT-3), GenBank Accession No. M37763; neurotrophin-4/5; Neurturin (NTN), GenBank Accession No. NP_004549; Neurotrophin-4, GenBank Accession No. M86528; Persephin, GenBank accession no. AAC39640; brain derived neurotrophic factor, (BDNF), GenBank accession no. CAA42761; artemin (ART), GenBank accession no. AAD13110; ciliary neurotrophic factor (CNTF), GenBank accession no. NP_000605; insulin growth factor-I (IGF-1), GenBank accession no. NP_000609; and Neublastin GenBank accession no. AAD21075.

A further example of a functional astrocytic phenotype is the enhancement of expression and/or secretion of a neurotrophic factor following addition of IL-1beta and cabergoline.

Astrocytes play an important role in the maintenance of low extra-cellular glutamate concentration by clearance of glutamate via high-affinity glutamate transporters. Therefore, another functional astrocytic phenotype of the cells of the populations of the present invention may be an increased activity of glutamate transporters. The activity of such glutamate transporters may be analyzed by measuring labeled aspartate (e.g. [$^3$H]-d-aspartate uptake from the culture medium of the cells.

As mentioned hereinabove a percentage of the cells of the cell populations of the present invention may additionally or alternatively comprise a structural astrocytic phenotype.

Examples of structural astrocytic phenotypes include a cell size, a cell shape, an organelle size and an organelle number. Thus, astrocytic structural phenotypes include a round nucleus, a "star shaped" body and many long processes that end as vascular foot plates on the small blood vessels of the CNS (See FIGS. 1A-B and 2A-D). Further examples of structural astrocytic phenotypes may be found in the following materials: Reynolds and Weiss, Science (1992) 255:1707-1710; Reynolds, Tetzlaff, and Weiss, J. Neurosci (1992) 12:4565-4574; and Kandel, et al., Principles of Neuroscience, third ed. (1991), Appleton & Lange, Norwalk, Conn. These structural phenotypes may be analyzed using microscopic techniques (e.g. scanning electro microscopy). Antibodies or dyes may be used to highlight distinguishing features in order to aid in the analysis.

A structural astrocytic phenotype may also comprise expression of an astrocyte marker.

As used herein the phrase "astrocyte marker" refers to a polypeptide which is either selectively or non-selectively expressed in an astrocyte. The astrocyte marker may be expressed on the cell surface or internally. Examples of astrocyte markers include S100 beta, glial fibrillary acidic protein (GFAP), glutamine sythetase, GLAST and GLT1.

As mentioned hereinabove, a percentage of cells of the cell populations comprise at least one mesenchymal stem cell phenotype which is not present in typical astrocytic cells. Such stem cell phenotypes are typically structural. For example, the cells of the present invention may show a morphology similar to that of mesenchymal stem cells (a spindle-like morphology). Alternatively or additionally the cells of the present invention may express a marker (e.g. surface marker) typical to mesenchymal stem cells but atypical to native astrocytic cells. Examples of mesenchymal stem cell surface markers include but are not limited to CD105+, CD29+, CD44+, CD90+, CD34−, CD45−, CD19−, CD5−, CD20−, CD11B− and FMC7−. Other mesenchymal stem cell markers include but are not limited to tyrosine hydroxylase, nestin and H-NF.

The cell populations of the present invention also include cells which display both an astrocytic phenotype and a mesenchymal stem cell phenotype. The mesenchymal stem cell phenotype is preferably not as astrocytic phenotype. Thus, as illustrated in Table 3, cells of the cell populations of the present invention were shown to express the mesenchymal stem cell markers, tyrosine hydroxylase, CD90 and H-NF, three markers which are known not be expressed in astrocytes.

Preferably, when cells comprise both the astrocytic and mesenchymal stem cell phenotypes described hereinabove, their astrocytic phenotype is unique to astrocytes. The cells may comprise a single astrocytic phenotype unique to astrocytes (e.g. star-shaped morphology) or a combination of non-unique astrocytic phenotypes which in combination represent a phenotype unique to astrocytes.

According to one embodiment of the present invention, the astrocytic phenotype of any of the cells of the populations of the present invention is as close as possible to native astrocytes. Thus, as illustrated in the Examples section below, the cells differentiated according to the method of the present invention represent an astrocyte like shape (FIGS. 1A-B and 2A-D), are accompanied by the presence of astrocyte markers (FIGS. 3A-B and 4A-B); express (FIG. 5, FIGS. 18A-I, FIGS. 19A-B and FIGS. 20A-C) and secrete (FIGS. 8A-D) significant levels of GDNF, BDNF and NGF; comprise NTF production which is further up-regulated by cabergoline a D2-receptor agonist and IL-1 (FIG. 7 and FIG. 8A); and possess glutamate-clearance machinery (FIG. 10).

The percentage of cells which comprise an astrocytic phenotype may be raised or lowered according to the intended needs. Thus for example, the cell populations may be enriched for cells with a particular astrocytic phenotype (e.g. expression of GDNF). This may be effected by FACS using an antibody specific for an astrocyte cell marker. Examples of such astrocytic markers are described hereinabove. If the cell marker is an internal marker, preferably the FACS analysis comprises antibodies or fragments thereof which may easily penetrate a cell and may easily be washed out of the cell following detection. The FACS process may be repeated a number of times using the same or different markers depending on the degree of enrichment and the cell phenotype required as the end product.

According to another embodiment of this aspect of the present invention the cell populations may be enriched for cells comprising both an astrocytic phenotype and a mesenchymal stem cell phenotype such that a homogeneous population of cells are generated.

Thus, according to yet a further aspect of the present invention there is provided an isolated human cell comprising at least one astrocytic phenotype and at least one mesenchymal stem cell phenotype, wherein the mesenchymal stem cell phenotype is not an astrocytic phenotype.

Once differentiated and optionally isolated, the cells may be tested (in culture) for their astrocytic phenotype (e.g. ability to secrete a functional neurotrophic factor). The cultures may be comparatively analyzed for an astrocytic phenotype, using biochemical analytical methods such as immunoassays, Western blot and Real-time PCR as described in Examples 1 of the Examples section which follows, or by enzyme activity bioassays.

According to the astrocytic phenotype, the cells and cell populations of the present invention may be used to treat a particular disease or disorder. The cell populations may be used directly following differentiation or may be enriched for a particular astrocytic phenotype as described hereinabove. As summarized in Table 1 hereinbelow, certain neurotrophic factors or set of neurotrophic factors have been shown to be particularly beneficial for treating a particular disease. For example, cells of the present invention which secrete NGF, BDNF, FGF and GDNF would be particularly suitable for treating Parkinson's.

TABLE 1

| Disease | Astrocytic phenotype | REF |
|---|---|---|
| Parkinsons | NGF, BDNF, FGF, GDNF | Walker DG, et al. Brain Res 1998; 794: 181-7.<br>Lorigados L, et al. Rev Neurol 1998; 26: 744-8.<br>Mogi M, et al. Neurosci Lett 1994; 180: 147-50.<br>Howells DW, et al. Exp Neurol 2000; 166: 127-35.<br>Beck KD, et al. Nature 1995; 373: 339-41.<br>Tomac A, et al. Nature 1995; 373: 335-9.<br>Gash DM, et al. Nature 1996; 380: 252-5.<br>Choi-Lundberg DL, Science 1997; 275: 838-41.<br>Bozzi Y, Borrelli E. Eur J Neurosci 1999; 11: 1275-84.<br>Chauhan NB, et al Soc Neurosci Abstr 1998; 24: 1465.<br>Chauhan NB, et al, Neurology 1999; 52: A212-213. |
| Epilepsy | BDNF, NGF, NT-3, glutamate transporter | G. W. Mathern. Mol. Chem. Neuropathol. 30 1-2 (1997), pp. 53-76.<br>Lucia Tapia-Arancibia et al. Frontiers in Neuroendocrinology 2004 Jul; 25(2): 77-107.<br>RYUTA KOYAMA and YUJI IKEGAYA; NEUROSCIENCE UPDATE 2005 Aug; 11(4): 282-7.<br>Gerald Seifert, et al., Nature Reviews Neuroscience 7, 194-206 (March 2006). |
| ALS | NT3, IGF1, BDNF, glutamate transporter | Luis H. Et al., Brain Research Reviews 2004 Dec; 47(1-3): 263-74.<br>Bradley WG. Ann Neurol 1995; 38: 971.<br>Haase G, et al. Nat Med 1997; 3: 429-36.<br>Arakawa Y, J Neurosci 1990; 10: 3507-15. |
| neuropathy | NGF | G. Sobue, M. et al. Neurochem. Res. 23 6 (1998), pp. 821-829. |
| Drug and alcohol addiction | GDNF | Ron D, Janak PH. Rev Neurosci. 2005; 16(4): 277-85. |
| Brain injury | Ability of cells to respond to IL-1 | Nancy Rothwell; Brain, Behavior, and Immunity. 2003 Jun; 17(3): 152-7. |
| Alzheimers | NGF BDNF | Crutcher KA, et al. J Neurosci 1993; 6: 2540-50.<br>Scott SA, et al. Nerve growth factor in Alzheimer's disease: increased levels throughout the brain coupled with declines in nucleus basalis. J Neurosci 1995; 15: 6213-21.<br>Peng S, et al. J Neuropathol Exp Neurol 2004; 63: 641-9.<br>Murer MG, et al. Neuroscience 1999; 88: 1015-32. |
| Huntingdon's | BDNF, NT-3, or NT-4/5 | Martinez-Serrano A, Bjorklund A. Trends Neurosci 1997; 20: 530-8.<br>Perez-Navarro E, et al. J Neurochem 2000; 75: 2190-9.<br>Perez-Navarro E, et al. Neuroscience 1999; 91: 1257-64. |
| Schizophrenia | NGF, NT-3, BDNF | Gal Shoval, Abraham Weizmana; Eur Neuropsychopharmacol. 2005 May; 15(3): 319-29.<br>Levi-Montalcini, R., 1987. Biosci. Rep. 7, 681-699.<br>Hattori, M., Nanko, S., 1995. Biochem. Biophys. Res. Commun. 209, 513-518.<br>Virgos, C., 2001, Schizophr. Res. 49, 65-71. |
| Optic nerve | CNTF | Paul A. Sieving, et al., Proc Natl Acad Sci USA. 2006 Mar 7; 103(10): 3896-901. |
| Stroke | FGF, BDNF | Wu D; Neuro Rx. 2005 Jan; 2(1): 120-8. |

It has been proposed that astrocyte cells may reduce the oxidative stress in neurons by metabolizing dopamine, as they express monoamine oxidase-B and catechol-O-methyl-transferase. Additionally, it has been proposed that astrocyte cells may be capable of preventing NO generated neurotoxicity by a glutathione dependent mechanism (Chen et al. 2004, Curr Drug Targets. 2005 November; 6(7):821-33). Accordingly, cells of the present invention which comprise a scavenging function and/or express dopamine metabolizing enzymes may also be suitable for treating Parkinson's.

Owing to insufficient clearance or decrease of the glutamate transporters glutamate excitotoxicity has been suggested as a causative factor for ALS [Bendotti 2001, et al, J Neurochem, 79(4):737-746, 2001]. Thus cells of the present invention which show an elevated glutamate transporter activity may also be suitable for treating ALS.

Thus, according to another aspect of the present invention there is provided a method of treating a CNS disease or disorder.

As used herein, the phrase "CNS disease" refers to any disorder, disease or condition of the central nervous system which may be treated with the cells of the present invention.

Accordingly, these cells can be used for preparing a medicament (interchangeably referred to as pharmaceutical composition), whereby such a medicament is formulated for treating a CNS disease or disorder.

Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, ALS, Multiple Sclerosis, Huntingdon's disease, autoimmune encephalomyelitis, diabetic neuropathy, glaucomatous neuropathy, macular degeneration, action tremors and tardive dyskinesia, panic, anxiety, depression, alcoholism, insomnia, manic behavior, Alzheimer's and epilepsy.

In any of the methods described herein the cells may be obtained from any autologous or non-autologous (i.e., allogeneic or xenogeneic) human donor. For example, cells may be isolated from a human cadaver or a donor subject.

The cells of the present invention can be administered to the treated individual using a variety of transplantation approaches, the nature of which depends on the site of implantation.

The term or phrase "transplantation", "cell replacement" or "grafting" are used interchangeably herein and refer to the introduction of the cells of the present invention to target tissue. The cells can be derived from the recipient or from an allogeneic or xenogeneic donor.

The cells can be grafted into the central nervous system or into the ventricular cavities or subdurally onto the surface of a host brain. Conditions for successful transplantation include: (i) viability of the implant; (ii) retention of the graft at the site of transplantation; and (iii) minimum amount of pathological reaction at the site of transplantation. Methods for transplanting various nerve tissues, for example embryonic brain tissue, into host brains have been described in: "Neural grafting in the mammalian CNS", Bjorklund and Stenevi, eds. (1985); Freed et al., 2001; Olanow et al., 2003). These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation.

Intraparenchymal transplantation can be effected using two approaches: (i) injection of cells into the host brain parenchyma or (ii) preparing a cavity by surgical means to expose the host brain parenchyma and then depositing the graft into the cavity. Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

For transplanting, the cell suspension is drawn up into the syringe and administered to anesthetized transplantation recipients. Multiple injections may be made using this procedure.

The cellular suspension procedure thus permits grafting of the cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20., 1976), by removing bone overlying the brain and stopping bleeding with a material such a gelfoam. Suction may be used to create the cavity. The graft is then placed in the cavity. More than one transplant may be placed in the same cavity using injection of cells or solid tissue implants. Preferably, the site of implantation is dictated by the CNS disorder being treated and the astrocytic phenotype comprised in the cell (e.g. particular neurotrophic factor being secreted) by the cells of the present invention. For example, cells secreting GDNF are preferably implanted in the sabstantia nigra of a Parkinson's patient.

Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the tissue or organ of interest. Thus, for example the cells may be administered directly into the brain as described hereinabove or directly into the muscle as described in Example 3 hereinbelow.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, 6-OHDA-lesioned mice may be used as animal models of Parkinson's. In addition, a sunflower test may be used to test improvement in delicate motor function by challenging the animals to open sunflowers seeds during a particular time period.

Transgenic mice may be used as a model for Huntingdon's disease which comprise increased numbers of CAG repeats have intranuclear inclusions of huntingtin and ubiquitin in neurons of the striatum and cerebral cortex but not in the brain stem, thalamus, or spinal cord, matching closely the sites of neuronal cell loss in the disease.

Transgenic mice may be used as a model for ALS disease which comprise SOD-1 mutations.

The septohippocampal pathway, transected unilaterally by cutting the fimbria, mimics the cholinergic deficit of the septohippocampal pathway loss in Alzheimers disease. Accordingly animal models comprising this lesion may be used to test the cells of the present invention for treating Alzheimers.

Survival and rotational behavior (e.g. on a rotarod) of the animals may be analyzed (as in Examples 2, 3 and 5) following administration of the cells of the present invention.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated Parkinson's patient will be administered with an amount of cells which is sufficient to alleviate the symptoms of the disease, based on the monitoring indications.

The cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA. Additionally, the cells of the present invention may be co-administered with other cells capable of synthesizing a neurotransmitter. Such cells are described in U.S. Pat. Appl. No. 20050265983 to the present inventors.

Following transplantation, the cells of the present invention preferably survive in the diseased area for a period of time (e.g. at least 6 months), such that a therapeutic effect is observed. As described in Example 2, the cells of the present invention were shown to be viable in the 6-OHDA lesioned mouse brain hemisphere at 16 weeks following transplantation and viable in the transgenic mouse model for ALS at 110 days post transplantation.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Characterization of Astrocyte-Differentiated BMSCs

Materials and Methods
Isolation and culture of human BMSC:
Bone marrow aspirations (10-30 ml) were collected from the posterior iliac crest of healthy adult human donors with informed consent. Low-density BM mononuclear cells (BM-MNC) were separated by FICOL-PAGUE density gradient (1.077 g/ml) and washed with HBSS. Next, the cells were plated in polystyrene plastic flasks in growth medium. Growth medium consisted of dulbecco's modified eagle's medium (DMEM) supplemented with 15% fetal calf serum (FCS), 2 mM L-glutamine, 100 µg/ml streptomycin, 100 U/ml penicillin, 12.5 units/ml nystatin (SPN). The non adherent cells were removed with medium replacement. Following confluence, adherent layers were trypsinized, reseeded, grown to confluence and passaged 2 to 6 times prior to experiments. Growth medium was changed twice a week and cells were maintained at 37° C. in a humidified 5% $CO_2$ incubator.

Astrocyte Differentiation:

To induce astrocyte differentiation, $1\times10^6$ cells were cultured in 10 mm dishes. Cells were replaced with pre-differentiation medium for 48 hours (DMEM supplemented with SPN, 2 mM L-glutamine, 20 ng/ml human epidermal growth factor HEGF (R& D, Systems, Minneapolis, Minn.), 20 ng/ml human basic fibroblast growth factor (hbFGF) and N2 supplement (insulin 5 µg/ml, progesterone 20 nM, putrescin 100 µM, selenium 30 nM, transferrin 100 µg/ml). After 48 hours, the pre-differentiation medium was changed to differentiation medium, (DMEM supplemented with SPN, 2 mM L-glutamine, 1 mM dibutyryl cyclic AMP dbcAMP, 0.5 mM isobutylmethylxanthine IBMX (Sigma-Aldrich, St. Louis, Mo., USA), 5 ng/ml human platelet derived growth factor PDGF (peprotech), and 50 ng/ml human neuregulin 1-β1 NRG1-β1-GGF-2). In some experiments IL-1β (100 pg/ml) or Cabergoline (130 pg/ml) were added into the medium 24 hours following initiation of differentiation.

Immunocytochemistry:

For immunochemistry analysis, cells were grown on 12 mm round poly-L-lysine coated glass coverslips. At the end of the experiment the medium was removed, cells were fixed with paraformaldehyde 4% (v/v) for 20 minutes at room temperature and permeabilized thereafter with 0.25% Triton X-100 (v/v) in 0.1M PBS for 20 minutes. Non-specific binding was blocked by incubating the cells in a 0.1M PBS solution containing 5% normal goat serum (NGS) and 1% bovine serum albumin (BSA) (Sigma) for 1 hour at 37° C. Subsequently, the cells were incubated in a 0.1M PBS solution containing 0.25% Triton X-100 (v/v), 5% NGS and 1% BSA with primary antibodies i.e. rabbit anti-glial fibrillary acidic protein (GFAP) 1:100 (DAKO), rabbit anti-GDNF 1:100 (Santa Cruz Biotechnology Inc., Santa Cruz, Calif., USA), mouse anti human nuclear h-Nuc 1:30, rabbit anti-Glutamine synthetase 1:200 (Sigma-Aldrich, St. Louis, Mo., USA), mouse anti S100β 1:200 (Sigma-Aldrich, St. Louis, Mo., USA). Secondary antibodies; for GDNF staining goat anti rabbit biotinylated (1:200) was added for 1 hour and subsequently streptavidine-Alexa-488 conjugated goat anti-rabbit IgG antibody 1:200 (Molecular Probes, Eugene, Oreg., USA). For other staining, Alexa-488 conjugated goat anti-rabbit IgG antibody 1:200 and Rodamine-Rx-conjugated 1:200 (Jackson ImmunoResearch Laboratories, West Grove, Pa., USA) were diluted in 0.1M PBS solution containing 0.25% Triton X-100 (v/v), 5% NGS and 1% BSA and were applied for 1 hour at room temperature. Nuclei were stained for 5 minutes with the nuclear dye DAPI 1:200 (Sigma, Aldrich). Following three rinses in PBS, the preparations were mounted in Antifaiding (Sigma, Israel) and examined using a fluorescent microscope coupled to a CCD camera (T.I.L.L. photonics, Martinsried, Germany). Excitation wavelengths (488, 405 and 568 nm for Alexa 488, DAPI and Alexa 568, respectively) were generated using a Xenon lamp coupled to a monochromator (T.I.L.L. photonics, Martinsried, Germany). Digital images were acquired using appropriate filters and combined using the TILLvisION software.

GDNF and BDNF Analysis:

At the end of the differentiating procedure described above, supernatant was collected from the plate and cells were harvested and counted. The amount of GDNF or BDNF in the cell's lysate and culture supernatants was quantified by using a GDNF or BDNF ImmunoAssay System (Promega) according to the manufacture's protocol. The absorbance at 450 nm was recorded on the Microplate Reader (BioRad Model 550) and the values were used to produce the curve of the GDNF or BDNF standard. The GDNF standard curve was linear between 15.6 and 1,000 pg/ml. ELISA results were calculated according to $10^6$ cells per plate.

Cell Count Assessment:

In order to determine the number of positive cells expressing a particular antigen, data were collected from careful examination of 15 fields from three independent cultures per sample. The total number of MSCs in these samples was determined by counting DAPI-stained cell nuclei and results are expressed as percentages of positive cells for either GDNF, glutamine synthetase, or S100β.

Preparation of mRNA:

Total RNA was isolated as described by Chomczynski and Sacchi (Anal Biochem 162:156-159, 1987). Cells were disrupted with 200 µl of solution D (4 M guanidinium thioyanate, 25 mM sodium citrate, 0.5% sarcosyl, 0.1 M 2-mercaptoethanol). Subsequently, 0.1 vol. of 2 M sodium acetate (pH 4), 1 vol. phenol (saturated) and 0.2 vol. of chloroform: isoamyl alcohol (49:1) were added. Samples were allowed to sit at 4° C. for 30 minutes, and then centrifuged at 10,000×g for 20 minutes at 4° C. The upper aqueous phase was mixed with 2 vols. of ethanol and the RNA was allowed to precipitate overnight at −20° C. The final RNA pellets were washed in 75% ethanol, and air dried. The pellets were dissolved in DEPC-treated water. The amount of RNA was determined spectrophotometrically using the ND-1000 spectrophotometer (Nano-drop). RNA quality was verified by measuring OD260/OD280 ratio. RNA was stored at −80° C. until used.

Real-Time Quantitative Reverse Transcription Polymerase Chain Reaction:

Real-time quantitative PCR of the desired genes was performed in an ABI Prism 7700 sequence detection system (Applied biosystems) using Sybr green PCR master mix (Applied biosystems) and the following primers: GAPDH sense- 5'-CGACAGTCAGCCGCATCTT-3' (SEQ ID NO: 1), GAPDH antisense 5'-CCAATACGACCAAATCCGTTG-3' (SEQ ID NO: 2); GDNF sense 5'-TCAAATATGCCAGAG-GATTATCCTG-3' (SEQ ID NO: 3), GDNF antisense 5'-GC-CATTTGTTTATCTGGTGACCTT-3' (SEQ ID NO: 4): BDNF sense 5'-AGCTCCGGGTTGGTATACTGG-3' (SEQ ID NO: 5), BDNF antisense 5'-CCTGGTGGAACT-TCTTTGCG-3' (SEQ ID NO: 6): GLAST sense 5'-AGAAT-GAGCTACC GGGAAGTCA-3' (SEQ ID NO: 7): GLAST anti sense 5'-CTAGC GCCG CCATTCCT-3' (SEQ ID NO: 8); NGF sense 5'-CATGCTGGACCCAAGCTCA-3' (SEQ ID NO: 9); NGF anti sense 5'-GACATTACGCTAT GCAC-CTCAGTG-3' (SEQ ID NO: 10); GFAP sense TAGAGGGCGA GGAGAACCG-3' (SEQ ID NO: 11); GFAP anti sense 5'GTGGCCTTCTGACACAGACTTG-3' (SEQ ID NO: 12); GLT-1 sense 5'-TTGGCTCAGAGGA ACCCAAG-3' (SEQ ID NO: 13), GLT-1 anti sense 5'-CAG-GATGACAC CAAA CACCGT-3' (SEQ ID NO: 14); S100 beta sense 5'-GGGTGAGACAAGGAAGAGGATG-3' (SEQ ID NO: 15), S100 beta anti-sense 5'-GCTTGTGCTT GTCTCCCTCC-3' (SEQ ID NO: 16); Glutamine synthetase sense 5'-CGAAGGCCTGCAGAGACC-3' (SEQ ID NO: 17), Glutamine synthetase anti sense 5'-AGGGTATACTCCT-GCTCCATGC-3' (SEQ ID NO: 18). GAPDH gene served as a valid reference 'housekeeping' gene for transcription profiling.

For quantitation, real time quantitative PCR (qPCR) was performed in duplicates. qPCR amplification was performed for each sample in separate wells of the same PCR reaction plate, which also contained standard curve for each gene amplified and no template controls (NTC). Optimal experimental parameters (hybridization temperature, elongation time, and primers concentration) were determined for each primer pair. For each gene, verifying a single peak in melting curve analysis assessed the specificity of the PCR product.

The PCR was performed in a total volume of 20 µl containing 1 µl of the above-described cDNA, 1 µl each of the 3' and 5' primers (final concentration of 500 nmol/L each), 10 µl of Absolute™ QPCR SYBR® Green ROX Mix and 8 µl of DEPC water.

The amplification protocol was 40 cycles of 95° C. for 15 sec followed by 60° C. for 1 min each. Quantitative calculations of the gene of interest versus GAPDH was performed using the ddCT method, as instructed in the user bulletin #2 ABI prism 7700 sequence detection system (updated October 2001).

Reverse Transcription Polymerase Chain Reaction (RT-PCR):

RT-PCR was carried out on 0.5 microgram RNA samples using the 10U enzyme RT-superscript II (Gibco-BRL, MD, USA) in a mixture containing 1.3 µM oligo-dT12-18 (Sigma, USA), 1× Buffer supplied by the manufacturer, 10 mM DTT, 20 µM dNTPs, and RNase inhibitor (RNAguard, amersham pharmacia biotech, UK). Reverse transcription was performed at 42° C. for 2 hours. PCR of the desired genes was performed with specific primers in a mixture containing 2 µl RT, 1× buffer (Takara, Japan), 200 µM dNTPs, 1 µM of each primer and 5U units of Taq polymerase (Takara, Japan) followed by 25-30 cycles in Thermocycler: 94° C. for 30 seconds, annealing 55° C. for 30 seconds and DNA extension at 72° C. for 45 seconds. Under these experimental conditions, linearity of the amplification was observed.

RT-PCR was performed on non-differentiated hBMSCs and the differentiated BMSCs according to the method of the present invention. Expression of the genes was compared between the two cell types and to expression in astrocytes (from information obtained from the literature). The primer sequences are detailed in Table 2 hereinbelow.

TABLE 2

| GENE | 5' PRIMER | 3' PRIMER | NCBI |
|---|---|---|---|
| CD90 | ctagtggaccagagccttcg<br>SEQ ID NO: 19 | gccctcacacttgaccagtt<br>SEQ ID NO: 20 | NM6288 |
| CD34 | aaggagcagggagcatac<br>SEQ ID NO: 21 | tgcatgtgcagactcctttc<br>SEQ ID NO: 22 | NM1773 |
| CD133 | gatgcagaacttgacaacg<br>SEQ ID NO: 23 | acacagtaagcccaggtagt<br>SEQ ID NO: 24 | NM006017 |
| Nestin | ccagaaactcaagcaccac<br>SEQ ID NO: 25 | ttttccactccagccatcc<br>SEQ ID NO: 26 | X65964 |
| H-NF | aaagcaccaaggactcact<br>SEQ ID NO: 27 | ttctcagacttctccaccac<br>SEQ ID NO: 28 | NM021076 |
| TH | gagggaaggccgtgctaaa<br>SEQ ID NO: 29 | gaggcgcacgaagtactcca<br>SEQ ID NO: 30 | NM000360 |
| NGFR | ctacggctactaccaggatg<br>SEQ ID NO: 31 | ctggctatgaggtcttgttc<br>SEQ ID NO: 32 | NM002507 |
| GDNF | tcaaatatgccagaggattatcctg<br>SEQ ID NO: 33 | gccatttgtttatctggtgacctt<br>SEQ ID NO: 34 | NM199231.1 |
| NGF | catgctggacccaagctca<br>SEQ ID NO: 35 | gacattacgctatgcacctcagtg<br>SEQ ID NO: 36 | NM002506.2 |
| IGF1 | tcagctcgctctgtccgtg<br>SEQ ID NO: 37 | ttgcgttcttcaaatgtacttcct<br>SEQ ID NO: 38 | NM000618 |
| BDNF | agctccgggttggtatactgg<br>SEQ ID NO: 39 | cctggtggaacttctttgcg<br>SEQ ID NO: 40 | NM170732.3 |
| CNTF | cctgactgctcttacggaatcctat<br>SEQ ID NO: 41 | cccatccgcagagtccag<br>SEQ ID NO: 42 | NM000614.2 |
| GFAP | tagagggcgaggagaaccg<br>SEQ ID NO: 43 | gtggccttctgacacagacttg<br>SEQ ID NO: 44 | NM003054 |
| S100b | gggtgagacaaggaagaggatg<br>SEQ ID NO: 45 | gcttgtgcttgtctccctcc<br>SEQ ID NO: 46 | NM006272.1 |
| NT3 Neurotrophin | gacttcagagaacaataaactcgtgg<br>SEQ ID NO: 47 | tgccaattcatgttcttccg<br>SEQ ID NO: 48 | NM002527.3 |
| GLAST | agaatgagctaccggaagtca<br>SEQ ID NO: 49 | ctagcgccgccattcct<br>SEQ ID NO: 50 | Nm004172.3 |
| GLUL | cgaaggcctgcagagacc<br>SEQ ID NO: 51 | agggtatactcctgctccatg<br>SEQ ID NO: 52 | NM02065.4 |

TABLE 2-continued

| GENE | 5' PRIMER | 3' PRIMER | NCBI |
|---|---|---|---|
| GLT1 | ttggctcagaggaacccaag SEQ ID NO: 53 | caggatgacaccaaacaccgt SEQ ID NO: 54 | D85884 |
| GAPDH | cgacagtcagccgcatctt SEQ ID NO: 55 | ccaatacgaccaaatccgttg SEQ ID NO: 56 | NM002046 |

Scanning Electron Microscopy:

The cells were fixed with 2.5% glutaraldehyde in phosphate buffer (pH 7.2), washed in the same buffer and post fixed with 2% OsO4. The third step of fixation was performed using a solution of tannic acid and guanidine hydrochloride. The triple-fixed cells were dehydrated in graded alcohol solutions. The alcohol was then exchanged for Freon-112 using graded Freon solutions. The cells were air-dried, gold coated and examined using a Jeol 840 scanning electron microscope.

Glutamate Uptake:

Functional characterization of glutamate transporters was performed on trypsinized differentiated cells. Transport velocity was estimated by measuring the uptake of [$^3$H]-d-aspartate (20 nM) following a six minute incubation at 37° C. in a buffer containing Na+. The specific activity of the glutamate transporters was expressed as the uptake velocity per the quantity of protein in mg.

Figure 1:
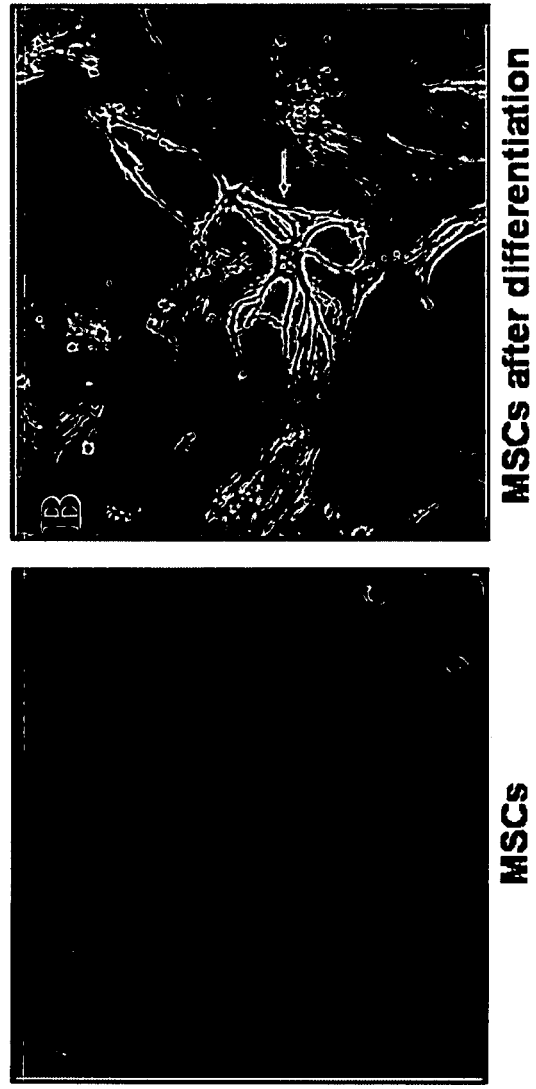
FIGS. 1A-B are light microscopy images of 5 day-differentiated and non-differentiated human MSCs. The differentiated human MSCs demonstrate astrocyte-like morphology such as the typicalastro-like structure. (light microscopy).
Figure 2:
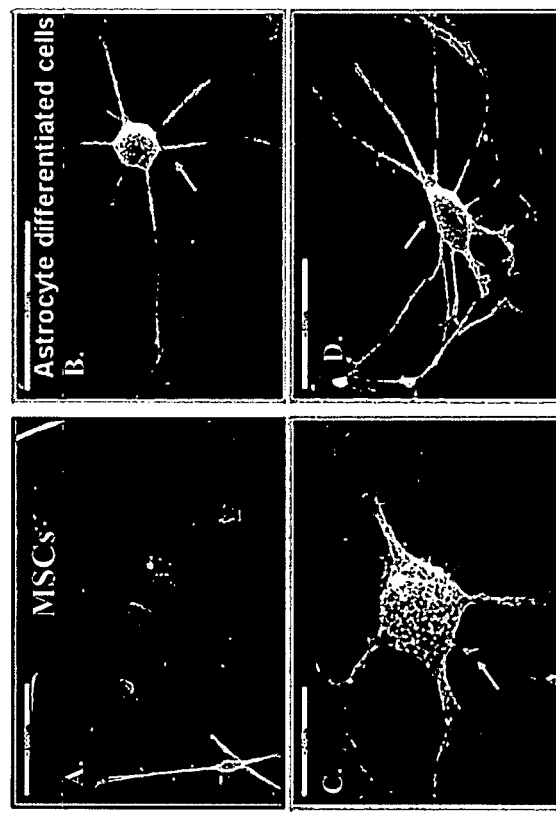
FIGS. 2A-D are scanning electro-microscopy images of 5 day-differentiated (FIGS. 2B-D) and non-differentiated (FIG. 2A) human MSCs. Differentiated human MSCs demonstrate astrocyte-like morphology.

Results hBMSc differentiated according to the method of the present invention acquired a satellite like morphology resembling astrocyte cells whereas the control cells that were grown in serum free medium alone, exhibited a flat fibroblast like morphology characteristic of hBMSc (FIGS. 1A-B). The differentiated cells were also analyzed using a scanning electromicroscope which confirmed their unique astrocytic satellite morphology (FIGS. 2A-D and 18B-C).

Figure 3:
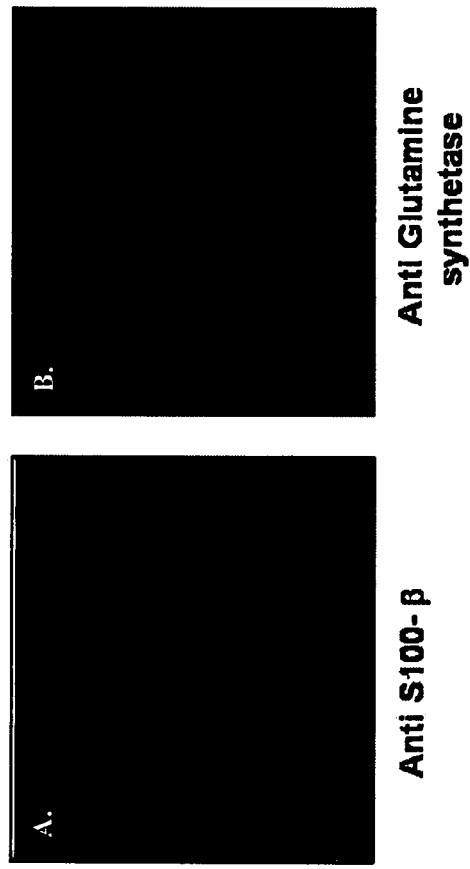
FIGS. 3A-B are photomicrographs illustrating the expression of astrocyte markers in the differentiated human MSC Immunostaining was preformed on differentiated human hBMSc with anti-S100β (FIG. 3A), and anti-glutamine synthetase (FIG. 3B). Cell nuclei were stained using DAPI (blue).
Figure 4:
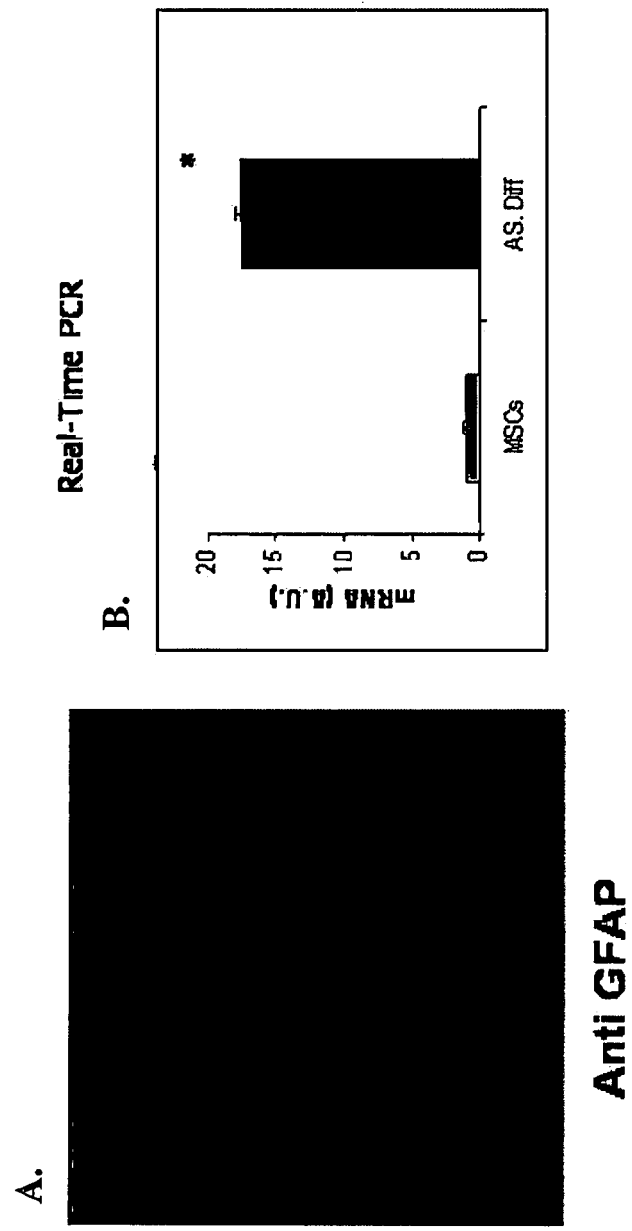
FIGS. 4A-B are photomicrographs are bar graphs illustrating the expression of the astrocyte marker glial fibrillary acidic protein (GFAP) in the differentiated human MSCs. Immunostaining was performed on differentiated human hBMSc with anti-GFAP and cell nuclei were stained using DAPI (blue) (FIG. 4A).

The astrocyte phenotype of the cells was further verified using immunofluorescence analysis with typical astrocyte markers. As illustrated in FIGS. 3A-B, the morphological change was accompanied with positive immunostaining for S100 beta, (a subunit of astrocyte Ca+ channels) and glutamine synthase (GS), (a unique astrocyte enzyme that catabolize glutamate). In addition, the cells stained positive for glial fibrillary acidic protein (GFAP) (FIG. 4A).

Quantification of the immunocytochemistry staining data revealed that the percentage of the positive cells for the S100 beta, GFAP and GS are in the range of 20-30%.

To further confirm the expression of astrocyitic markers, real-time PCR analysis was performed. As demonstrated in FIG. 4B, the GFAP transcript was up-regulated by 10-20 fold. Similar values were shown in S100 beta and GS transcripts.

Figure 5:
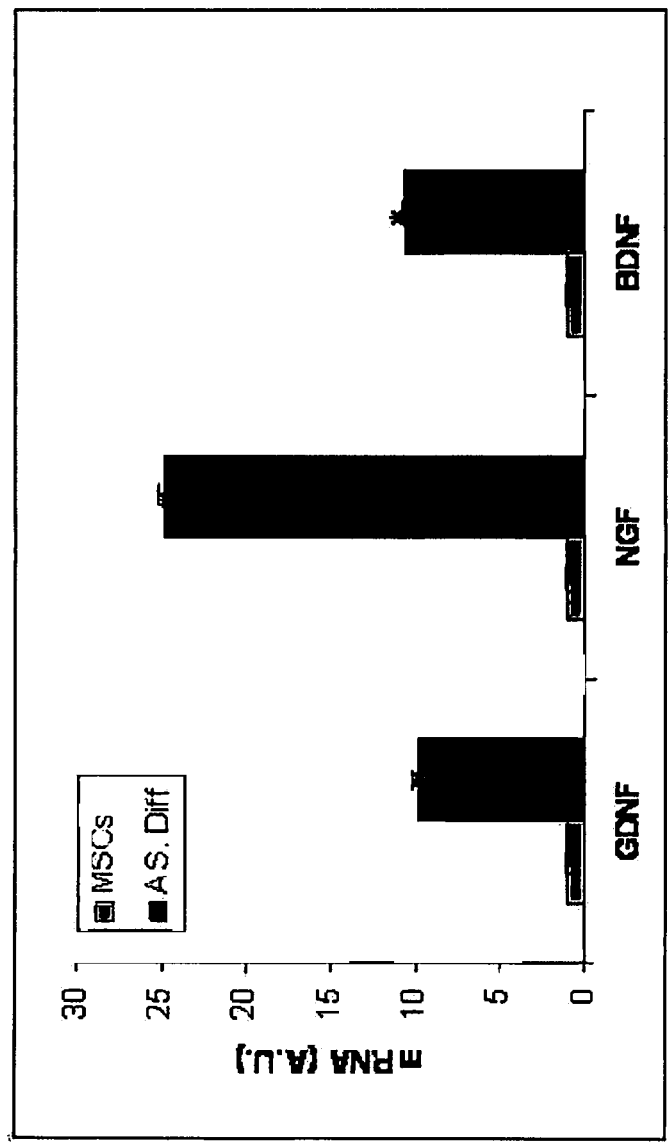
FIG. 5 is a bar graph illustrating the amounts of neurotrophic factors transcripts in differentiated human MSCs compared to non-differentiated human MSCs. Cell extracts were subject to real time PCR assay for GDNF (SEQ ID NOs: 3 and 4), NGF (SEQ ID NOs: 9 and 10) and BDNF (SEQ ID NOs: 5 and 6) transcripts.
Figure 6:
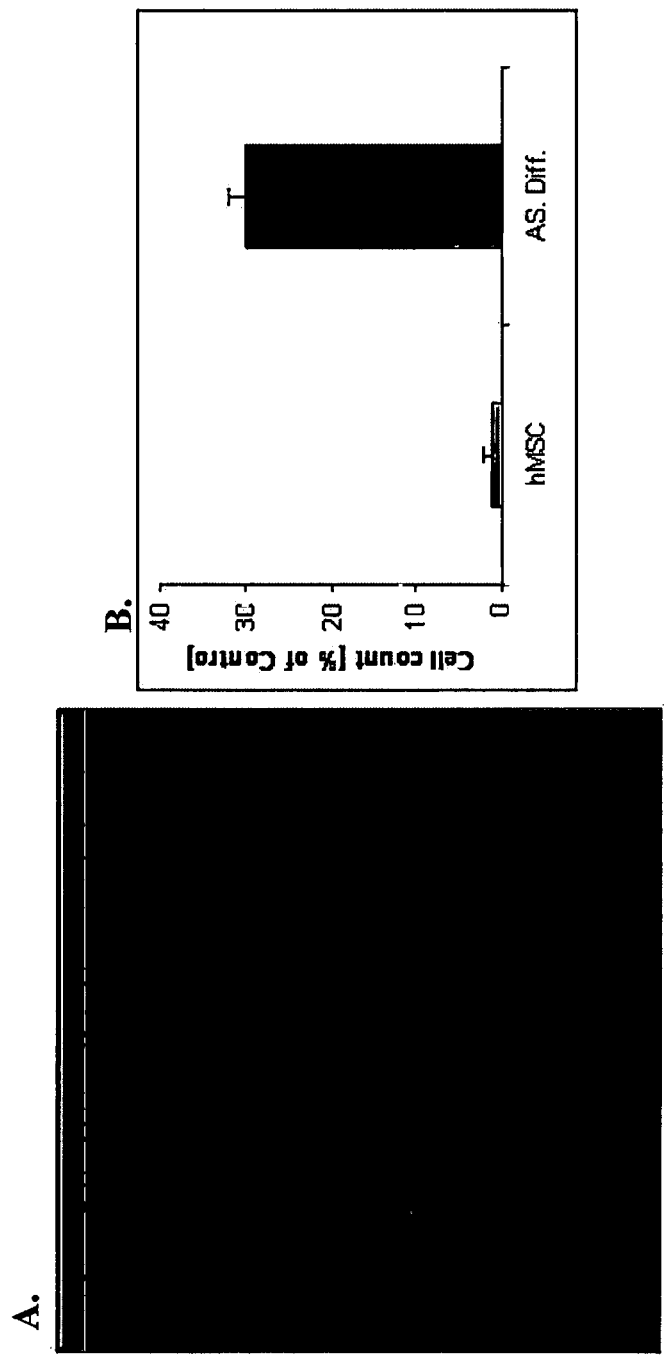
FIGS. 6A-B are photomicrographs and bar graphs illustrating the expression of GDNF on the differentiated human MSCs. Immunostaining was performed on differentiated human hBMSc with anti-GDNF. Cell nuclei were stained using DAPI (blue) (FIG. 6A).

Since astrocytes are known for their secretion of neurotrophic factors (NTFs), the mRNA levels of NTFs such as GDNF, NGF and BDNF were analyzed. Real time PCR analysis revealed that astrocyte differentiated hBMSc expressed high quantities of NTFs transcripts as compared to low or absence of these transcripts in MSC grown in serum free medium (FIG. 5 and FIG. 19A). Immunostaining with anti-GDNF revealed 30% of the cultured cells positively stained with the antibody (FIGS. 6A-B). Further immunostaining studies confirmed that the astrocyte differentiated hBMSc also express NGF, BDNF, CNTF (FIGS. 18A-I) and IGF (FIG. 19B). Costaining with more than one antibody, revealed that the astrocyte differentiated hBMSc of the present invention co-express GDNF and glial fibrillary acidic protein (GFAP)

An ELISA assay with specific antibodies was used to quantify the production and secretion of NTFs. Measurement of GDNF production was tested in the cell extract (FIG. 7) and in the growth medium FIG. 8A. Although a basal level of GDNF production was detected in the cultured MSC and neuroblastoma cell line (SH-SY5Y treated with rasagelein), in the culture media GDNF was detected only in the differentiated MSC.

Moreover, a marked enhanced production and secretion of GDNF was detected following addition of IL-1beta and cabergoline, factors which are known to upregulate GDNF. This phenomenon supports the notion that the differentiated cells respond as astrocytes. The levels of secreted GDNF and NGF were compared in several donors and it can be seen that the levels of secretion vary between 69-140 pg/10$^6$ cells for GDNF (FIG. 8B) and 356-875 pg/10$^6$ cells for NGF (FIG. 8C).

Figure 9:
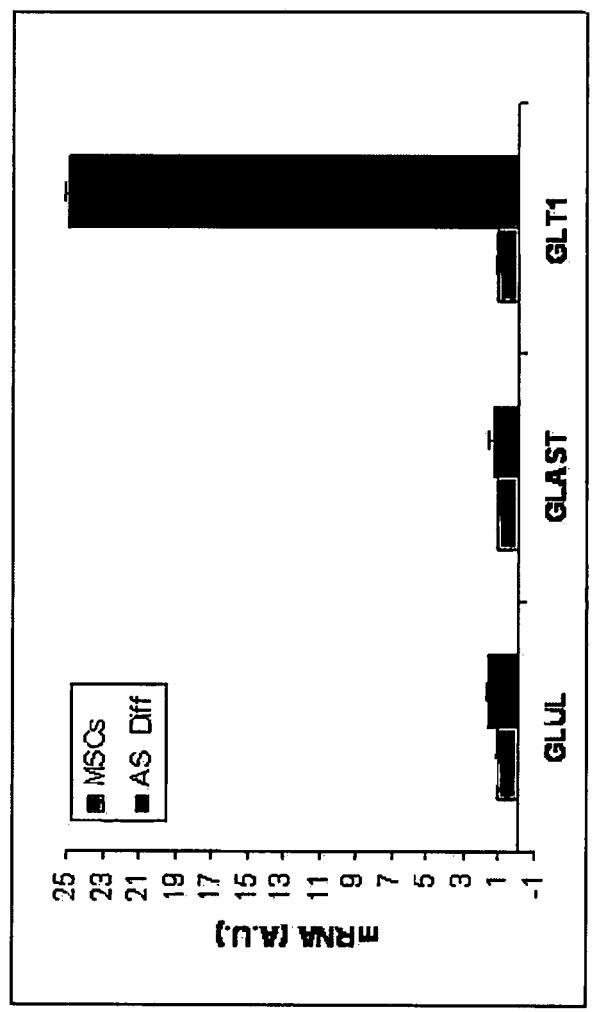
FIG. 9 is a bar graph illustrating the expression of the glutamate transporters GLAST and GLT-1 following differentiation of MSCs. The expression of these glutamate transporters was evaluated by Real Time-PCR performed on total RNA extracted from hBMSc grown in serum free medium and astrocyte differentiated hBMSc. Primers for GLAST were SEQ ID NOs: 7 and 8 and primers for GLT-1 were SEQ ID NOs: 13 and 14. Samples were also used in PCR amplification of the GAPDH allowing a quantitative analysis of PCR products expressed in arbitrary units (mean±SEM from triplicate measures performed on independent cultures). Statistical analysis was performed by one-way anova followed by the Newman-Keul's test for multiple comparisons. *(p<0.05) denote significant differences from cells maintained in the serum free medium.

Astrocytes play an important role in the maintenance of low extra-cellular glutamate concentration by clearance of glutamate via high-affinity glutamate transporters and catabolizing it by glutamine synthetase. Therefore, the differentiated cells were analyzed, using RT-PCR analysis for expression of glutamate transporters and glutamine synthetase. A high expression of GLT-1/EAAT-2 transcript was found in astrocyte differentiated hBMSc (FIG. 9). The activity of the glutamate transporter was evident by the $^3$H-glutamate uptake from the culture medium of the differentiated cells but not from the MSC (p<0.005) (FIG. 10).

A more detailed RT-PCR analysis was performed in order to determine which mesenchymal cell and which astrocytic cell markers were expressed by the cells of the present invention. The expression of the genes was in the two cell types was also compared to expression of the genes in astrocytes (information obtained from the literature). The results are summarized in Table 3 hereinbelow.

TABLE 3

| GENE | hMSc | DIF | Astrocyte |
|---|---|---|---|
| CD90 | + | + | − |
| CD34 | − | − | − |
| CD133 | − | − | − |
| Nestin | ++ | + | +/+++/− |
| H-NF | + | + | − |
| TH | + | + | − |
| NGFR | + | + | +++ |
| GDNF | + | ++ | +++ |
| NGF | + | +++ | +++ |
| IGF1 | + | ++ | +++ |
| BDNF | + | ++ | +++ |
| CNTF | ND | ND | +++ |
| GFAP | + | +++ | +++ |
| S100b | + | ++ | +++ |
| NT3 Neurotrophin | + | + | +++ |
| GLAST | + | ++ | +++ |
| GLUL | + | ++ | +++ |
| GLT1 | + | ++ | +++ |
| GAPDH | + | + | + |

Thus, it can be seen that the differentiated cells of the present invention show a specific phenotype that is different to both mesenchymal stem cells and astrocytes. For example, the cells of the present invention express of CD90, tyrosine hydroxylase and H-NF differentiating them from astrocytes. In addition, the cells of the present invention express high levels of neurotrophic factors and astrocyte markers, differentiating them from mesenchymal stem cells.

Example 2

Intrastriatal Transplantation of Astrocyte-Like Differentiated hBMSc Improve the Motor Functions of Lesion Rats In order to explore the possible therapeutic potential of the cells of the present invention, HBMSCs differentiated according to the method of the present invention were transplanted in an established rat model of Parkinson disease.

Materials and Methods

Animals:

Male Sprague-Dawley rats (Harlan, Israel) weighing 220-280 g were used for the 6-OHDA-lesion experiment. All animals were housed in standard conditions; constant temperature (22±1° C.), humidity (relative, 30%), 12-h light: 12-h dark cycle and free access to food and water. Surgical procedures were performed under the supervision of the Animal Care Committee at the Rabin Medical Center and at Tel Aviv University, Tel Aviv, ISRAEL.

6-OHDA Lesions:

Rats were anaesthetized with chloral hydrate, 350 mg/kg i.p., and secured in a stereotaxic frame (Stoelting, USA). Animals were unilaterally injected with 6-OHDA hydrobromide (12 μg/6 μl dissolved in ascorbate-saline) using Hamilton 10 μl syringe with a 26-gauge needle, into the left striatum at the two sites (6 μl per each site in two depth). The coordinates of the injections were as follows: (1) AP: +0.5, mm from bregma, L: −2.5, mm lateral to middle, V: −6.5 mm ventral to the dural surface, and (2) AP: −0.5 mm, L: −3.7 mm, V: −6.0 mm, based on the stereotaxis atlas (Paxinos & Watson, 1986). At the completion of the injection, the cannula was left in place for another 3 minutes before being withdrawn at 1 mm/min in order to prevent a vacuum.

Measurement of Rotational Behaviour:

Lesioned rats were tested for rotation behavior 14 days following the intracerebral injection of 6-OHDA. Motor asymmetry was monitored in an automated rotation-measuring apparatus for 1 hour following subcutaneous injection of the DA agonist apomorphine (Sigma, 0.15 mg/kg, dissolved in normal saline). Apomorphine induces contralateral turning behavior to the original lesion side because the striatal DA receptors become hypersensitive as a result of the 6-OHDA lesion. Rats with a rotation rate of five turns per minute were considered to be an established PD model and were used for grafting experiments. This test is widely used as a reliable index of dopamine depletion in the striatum.

Transplantation:

Six weeks following the 6-OHDA lesion, the PD model rats were divided into two groups, a control group and an experimental group. Rats in the control group (n=7) were injected with 0.9% Saline. Rats in the experimental group (n=6) were grafted with GDNF-producing cells. hBMSC astrocyte like cells were harvested prior to transplantation and resuspended at $5\times10^5$ vital cells/5 μl in saline. The cells were stereotactically injected into the left striatum in one site at the two depth (2.5 μl per each) through a 26-gauge needle of a 10 μl Hamilton syringe. The coordinates used for injection were as follows: (1) AP: +1.0 mm, L: +3.0 mm, V: −5.0 mm; and (2) AP: +1.0 mm, L: +3.0 mm, V: −4.1 mm, with the tooth-bar set at the level of the interaural line. After the operation, the animals were subjected to rotation tests every two week as described above. In the case of human MSC transplantation, animals were immunosuppressed by subcutaneous injection of Sandimune (10 mg/kg/day; Novartis) every day.

Rotor-Rod:

Performance on a rotorod task was tested at 3 months post transplantation. The task consisted of three consecutive trials in which the rat were placed on the rod and challenged (until 16 RPM) to prevent themselves from falling off the accelerating rod. Each trial was continued up to a maximum of 2 minutes. The interval between trials was 30 seconds. The results were obtained from two weekly tests.

Sun Flower Test:

The purpose of this test was to challenge the animals to open sunflowers seeds during a maximum time of 5 minutes. In order to perform the test animal were denied excess food and supplied with only 45 mg/gk/day three days prior to initiation of monitoring. Animals were trained for 3 days and on the fourth and fifth day, measurements were taken. The animals were placed in empty cages and supplied with seeds for 5 minutes. The number of open and eaten seeds was measured. [Gonzalez C., Kolb B. A comparison of different models of stroke on behavior and brain morphology. E. J. Neuroscience 18 (1950-1962), 2003].

Immunohistochemistry:

At 16 weeks following transplantation both the control and treatment groups were subjected to immunostaining. Rats were deeply anaesthetized with chloral hydrate (350 mg/kg i.p) and perfused transcardially with 65 ml of cold saline, followed by 250 ml of cold 4% paraformaldehyde in 0.1 mol/l PBS (pH 7.4). Brains were removed, placed in 4% PFA/PBS for 48 hours, followed by cryoprotection in 20% sucrose/PBS for 48 hours, and then frozen in isopentane on dry ice. Serial coronal sections of the brain were cut at 20 μm thickness on a microtome cryostat. The sections were washed 3 times in PBS, and subsequently blocked in 5% normal horse serum (Biological Industries) in PBS for 1 hour. Subsequently, the sections were incubated for 24 hours in the same solution containing primary antibodies against human nuclei (1:30; mouse monoclonal; Chemicon International, Temecula, Calif., USA), against GDNF (1:200; rabbit polyclonal, Santa Cruz) and against GFAP (1:100, rabbit DAKO). Sections were then washed three times in PBS and exposed to secondary antibodies: goat anti-mouse IgG (1:500; Jackson Immuno Research Laboratories Inc., West Grove, Pa., USA) coupled to rhodamine; and goat anti-rabbit IgG conjugated to Alexa-488 (1:500 Molecular Probes, Eugene, Oreg., USA) applied for 1 hour at room temperature. Nucleii were stained for 5 minutes with the nuclear dye DAPI 1:200 (Sigma). Finally, sections were rinsed in 0.1 M PBS and coverslipped with 95% glycerol. Control immunostaining experiments were carried out by either omitting: (i) primary antibody, (ii) secondary antibody, and (iii) both primary and secondary antibodies.

Figure 11:
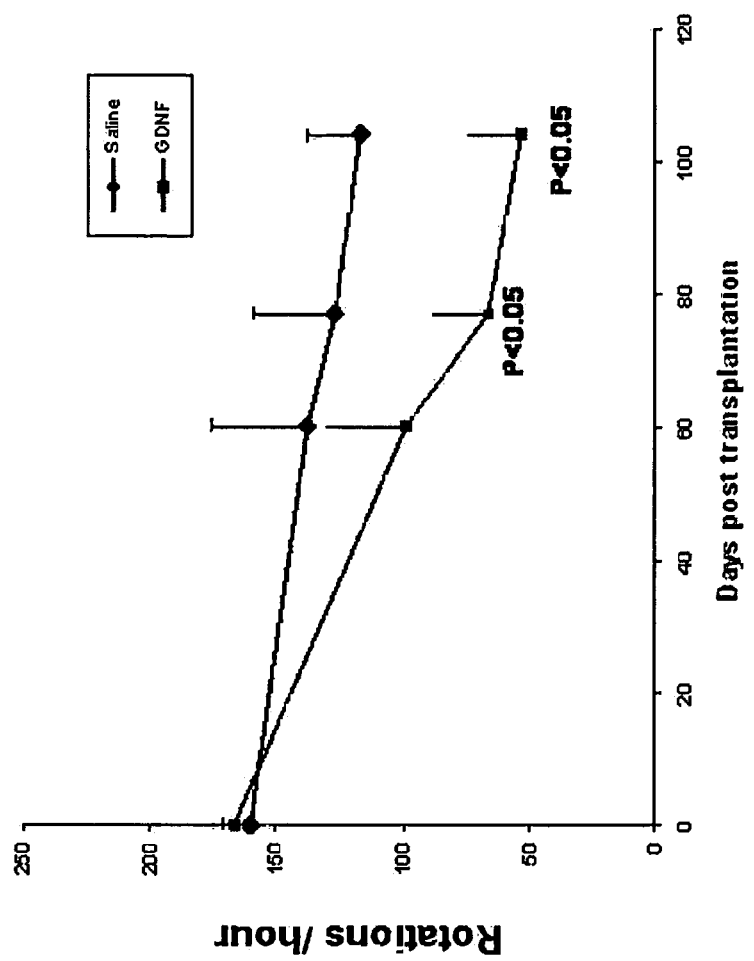
FIG. 11 is a line graph illustrating the improvement in behaviour of 6-OHDA lesioned rats transplanted with astrocyte differentiated hBMSc. Rats were transplanted with 5×10$^5$ cells injected into the ipsilateral striatum 6 week post lesion. Turning behaviour induced by apomorphine (0.15 mg/kg, s.c.) was recorded for a mean number of turns per 60 minutes. Transplanted rats exhibit a marked (p<0.05) decrease in rotations 75 days post transplantation.

Results 6-hydroxydopamine was injected intra striatally into rat brains to induce moderate damage of the dopaminergic neurons in the striatum. The extent of the lesion was measured three weeks later by injection of apomorphine leading to the ipsilateral rotations. Astrocyte-like cells ($5\times10^5$) were grafted into the ipsilateral striatum of rats that were preselected based on their rotational performance. Pharmacological-induced rotational behavior was measured in transplanted rats as well as in saline injected rats at 60, 75 and 105 days following engraftment. During the experiment, both groups were injected daily with cyclosporine in order to prevent graft rejection. As illustrated in FIG. 11, apomorphine-induced rotations decreased from an average of 160 rotations per hour at baseline to 60 rotations per hour at 75 days in transplanted rats (n=8), and 50 rotations per hour 105 days following transplantation (68% and 75% reduction p<0.05). The control group (n=8) rotated 155 times per hour at baseline and 140 after 105 days (no significant reduction).

Figure 12:
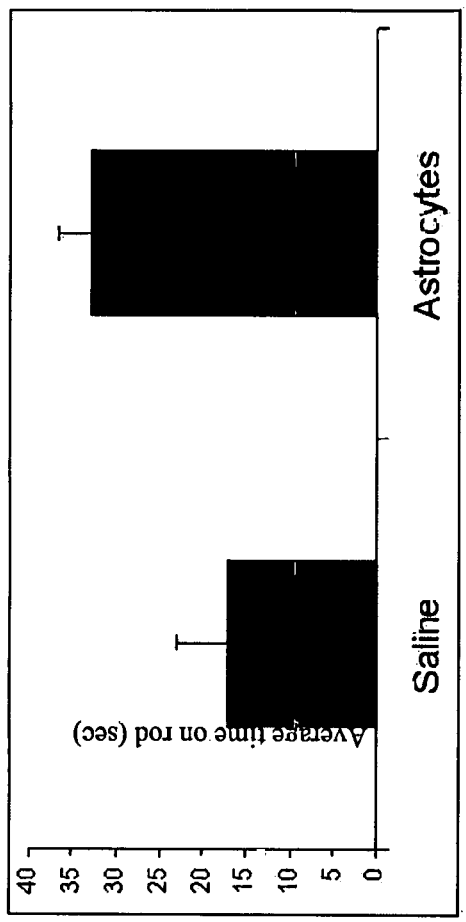
FIG. 12 is a bar graph illustrating the improvement in rotarod assay of 6-OHDA lesioned rats transplanted with astrocyte differentiated hBMSc. Rotarod performance (seconds on the rod) was observed 95 days post-grafting in the same rats. Transplanted rats exhibit a marked (p<0.05) improvement (multiple comparisons tests after Friedman anova, P<0.05).

95 days following transplantation, a non-pharmacological rotor-rod test was performed in order to provide direct measurement of motor deficits. Animals transplanted with the astrocyte-like cells were able to walk for a longer period on the accelerating rod than the control (FIG. 12).

Figure 13:
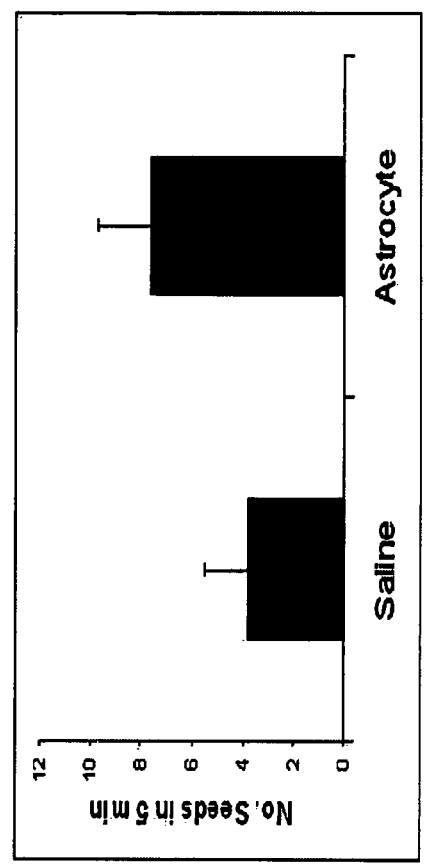
FIG. 13 is a bar graph illustrating the improvement in delicate motor function of 6-OHDA lesioned rats transplanted with astrocyte differentiated hBMSc. A sunflower seed eating test was performed 100 days post transplantation. Astrocyte transplanted rats opened and ate the seeds during a 5 minute period much faster as compared to saline treated rats. Results are mean±SEM of two tests performed in two following days.
Figure 14:
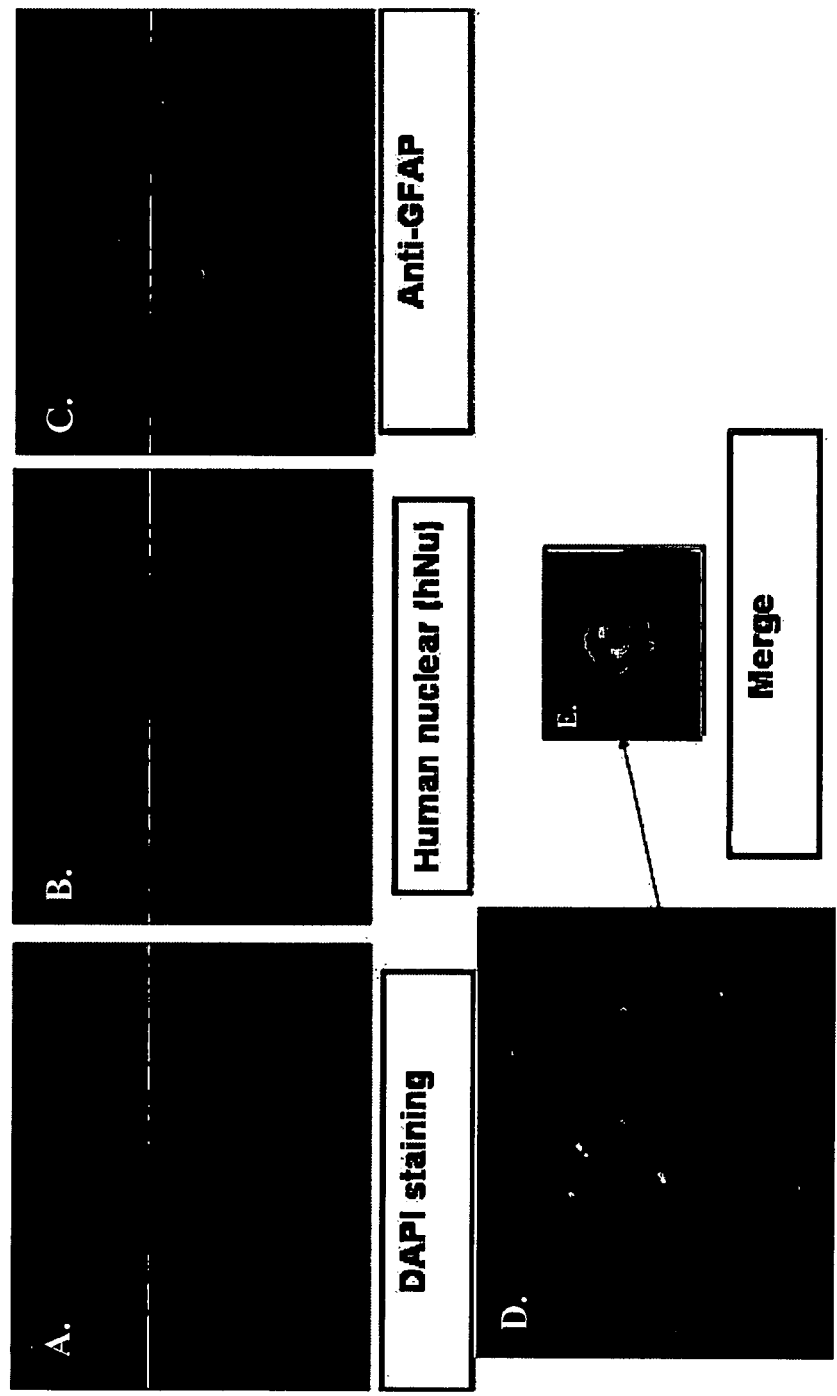
FIGS. 14A-E are confocal microscopy images on cells of 6-OHDA lesioned rats transplanted with astrocyte differentiated hBMSc. At 110 days post transplantation the animals were sacrificed and histology studies were performed.

The sun flower eating test was also applied to the animals. At day 100 following transplantation animals were evaluated for their ability to open sun flower seeds in a limited time (see methods). The transplanted animals opened 44 seeds in 5 minutes compared to control that opened 44 in the same time (p<0.05) (FIG. 13).

At 110 days following transplantation the animals were sacrificed and histology studies were performed in order to identify and characterize the transplanted cells. Anti-human nuclear antigen and anti-GFAP antibodies were used to identify the transplanted differentiated cells (FIGS. 14A-E). Immunostaining and confocal microscopy studies revealed that up to 25% of the cells that were positive for human antigen were also positive for GFAP. These results indicate that the astrocyte-like cells are capable of restoring the dopamine deficit in the striatum and are probably of benefit in other neurodegenerative disease.

Example 3

Intramuscular Transplantation of Astrocyte-Like Differentiated hBMSc Improve the Motor Functions of a Transgenic Mouse Model of ALS Materials and Methods
Animal Model:
The colony of TgN(SOD1-G93A)1Gur transgenic mice (Gurney 1994) was obtained from the Jackson Laboratory (USA). The mice were bred in CSJLF1 and at one month of age offspring was genotyped by PCR analysis, using the following PCR primers: hSOD1 upstream primer (SEQ ID NO: 19) 5'CTAGGCCACAGAATTGAAAGATCT3'; hSOD1 downstream primer (SEQ ID NO: 20) 5'GTAGGTG-GAAATTCTAGCATCATCC3'; IL2 upstream primer (SEQ ID NO: 21) 5'CATCAGCCCTAATCCATCTGA3'; IL2 downstream primer (SEQ ID NO: 22) 5'CGCGACTAA-CAATCAAAGTGA3'. The annealing temperature was 53° C., the PCR products 236 bp (hSOD1), 324 bp (IL2). Mice to be used in this study were healthy until 3 months of age and became completely paralyzed between 4 and 5 months of age. Animal experiments were approved and supervised by the Tel-Aviv University.

Cell Transplantation and Behavior:
On day 40, $0.5 \times 10^6$ human astrocyte differentiated cells (prepared as described in Example 1) were transplanted intra gastrocnemius muscle in two legs. The motor performance was evaluated every two week by a rotarod apparatus with accelerated rotations.

Histopathological Evaluation:
Mice were sacrificed at day 110 and the legs were placed in 4% paraformaldehyde 0.1 M phosphate buffer, pH 7.4, 4° C. Paraffin blocks were prepared and immunostained with anti human antigens antibodies.

Statistical Analysis:
Comparisons were made by ANOVA with post hoc Dunnett test when more than two groups were involved. If data was not normally distributed, a nonparametric test (Mann-Whitney U-test) was used for the comparisons of results. Data was expressed as mean±s.e.m.

Results
The astrocyte differentiated cells ($0.5 \times 10^6$) were transplanted on day 40, into the hmSOD mice (n=8) intra muscle (feet). Parallel group was injected with saline. In addition wild type mice (n=8) and mhSOD Tg mice (n=8) were used as positive and negative controls.

Figure 15:
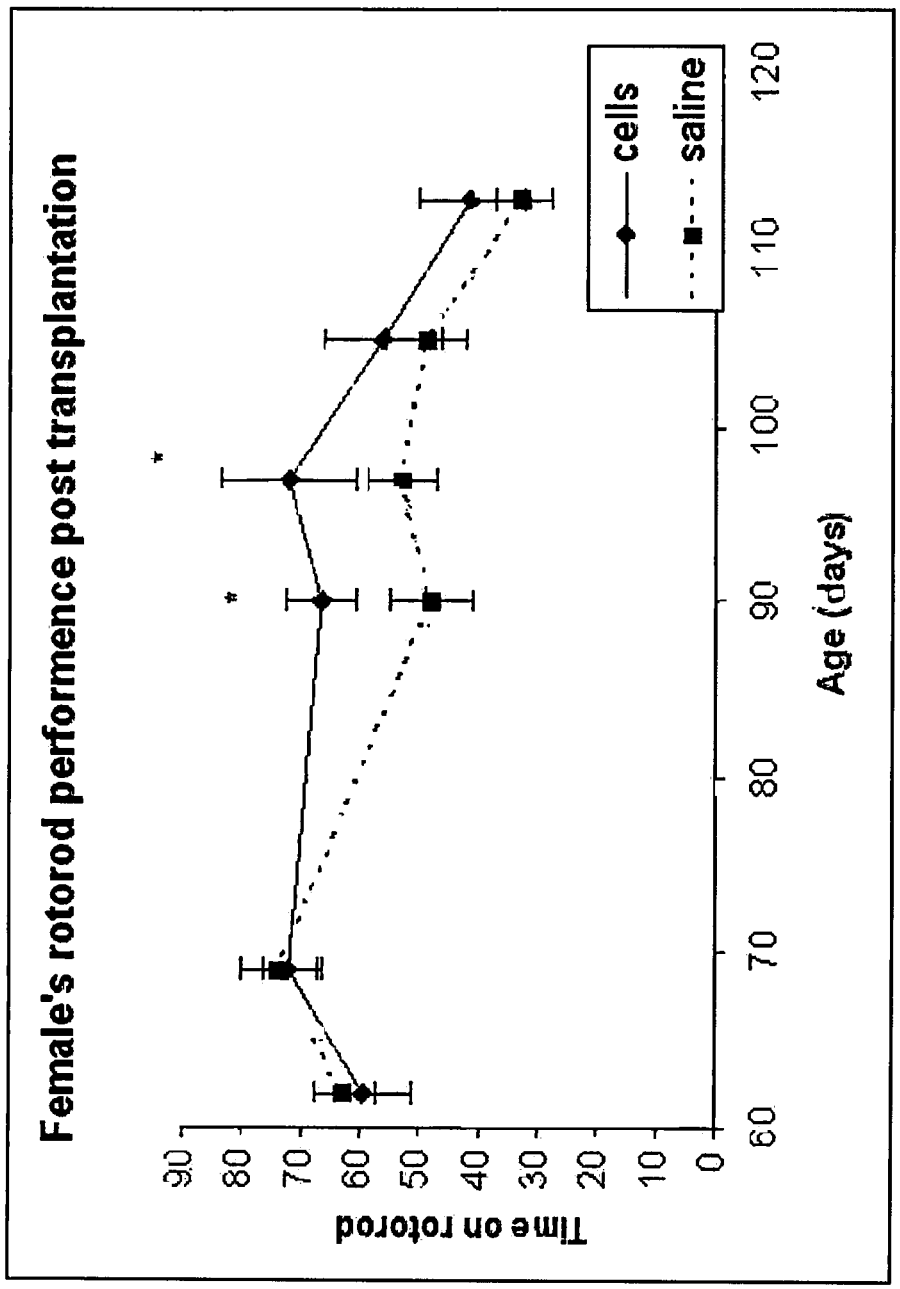
FIG. 15 is a line graph illustrating that astrocyte differentiated BMSCs transplanted into the gastrocnemius of ALS mice delay the disease onset and improve their motor performance on rotarod (n=8, p<0.05).

The behavioral assessment was performed on rotarod (see M&M) from day 40 and up till death (day 120-140) every two weeks. As seen in FIG. 15, the reduction in motor performance (i.e. the ALS symptoms) was significantly delayed in the cell-transplanted mice.

Figure 16:
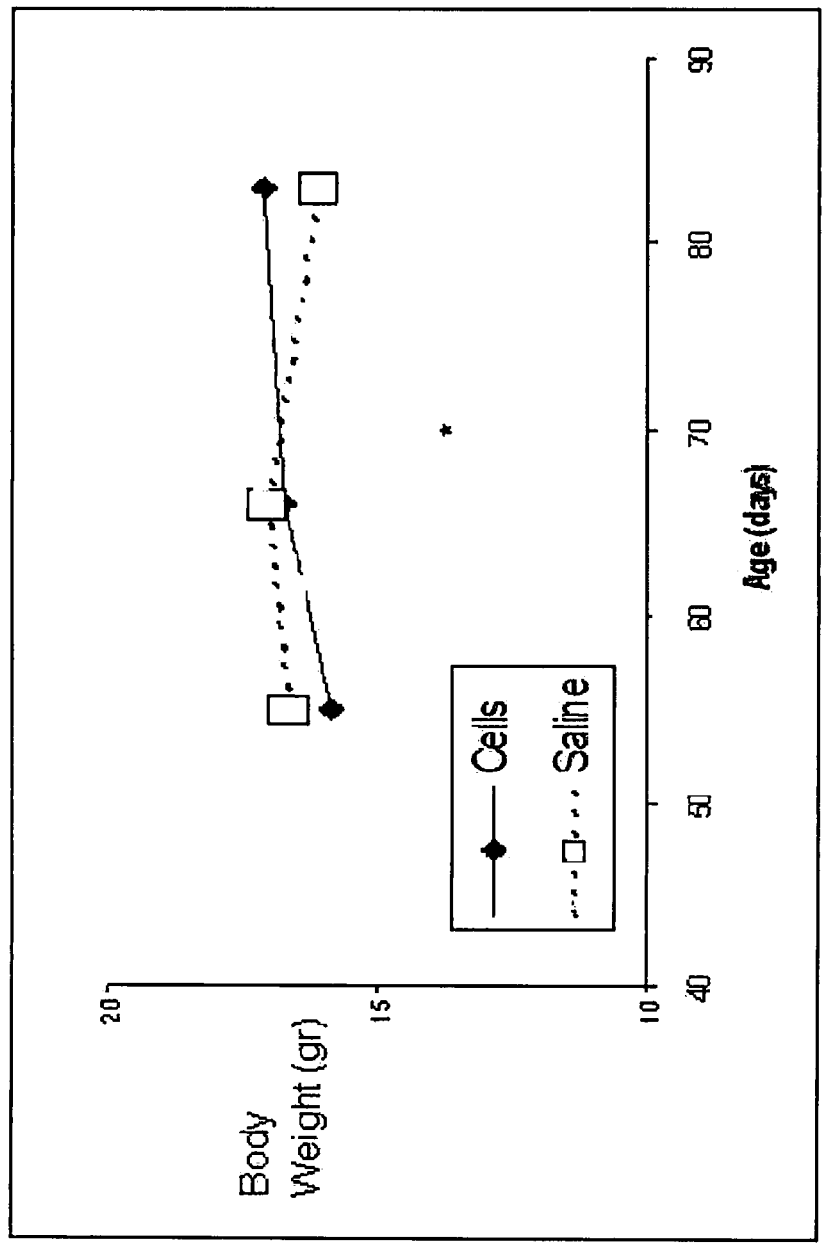
FIG. 16 is a line graph illustrating that astrocyte differentiated BMSC transplanted into the gastrocnemius of ALS mice delay the body weight decline.

Animal weight was measured and compared between the transplanted group and the controls and statistically analyzed. The control group showed a significantly greater (p<0.05) weight reduction than the transplanted group (FIG. 16).

A histological study that was performed on day 110 with anti-human nuclear antigen antibodies indicated that the engrafted cells survived (FIG. 17A-C).

Example 4

Intrastriatal Transplantation of Differentiated Human MSC Reduces Rotational Behavior in a Mice PD Model Materials and Methods
The effect of the astrocyte differentiated hMSC was examined in the 6-OHDA lesion model of PD induced in mice. Four weeks post unilateral intrastriatal injection of 6-OHDA, saline or differentiated hMSC ($2.5 \times 10^5$) were engrafted into the ipsilateral striatum. During the three-month post transplantation, the percentage of amphetamine-induced rotations was recorded and compared to the number of rotations of each performed before the saline injection or cell transplantation.

Figure 21:
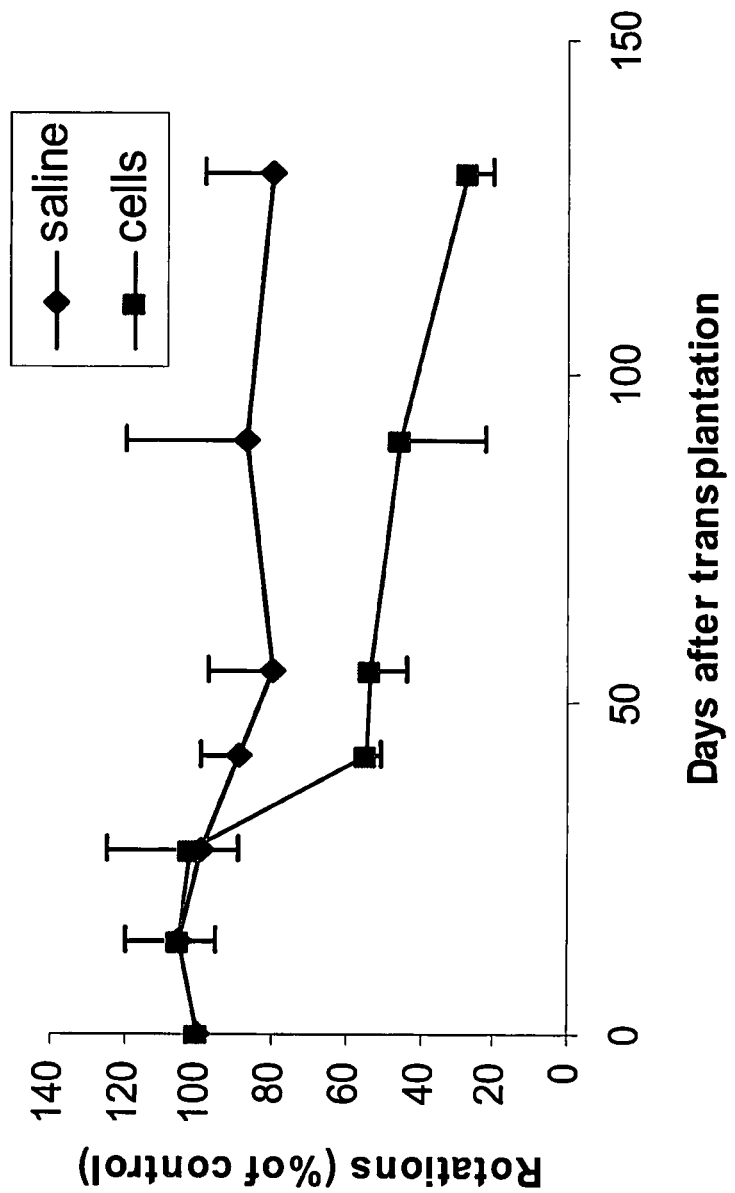
FIG. 21 is a graph illustrating that 6-OHDA lesioned mice transplanted with astrocyte-differentiated human BMSC demonstrate improved motor performance. Mice were transplanted with $2.5 \times 10^5$ astrocyte-differentiated cells, injected into the ipsilateral striatum 4 week post lesion. The amphetamine-induced (0.5 mg/kg, i.p.) rotation test was recorded for average number of turns performed by group per 30 min. Rotations were compared with base-line performance measured twice before transplantation.

Results
In the saline group, the mice demonstrated stable response to amphetamine for 130 days post saline injection up to 20% of the initial rotation rate (FIG. 21).

Example 5

Intramuscular and Intracereberal Transplantation of Astrocyte-Like Differentiated hBMSc Improve the Motor Functions of a Transgenic Mouse Model of ALS Materials and Methods
Cell Transplantation and Behavior:
On day 40, $0.5 \times 10^6$ human astrocyte differentiated cells (prepared as described in Example 1) were transplanted intra gastrocnemius muscle in two legs and intracerebrally. The motor performance was evaluated every two week by a rotarod apparatus with accelerated rotations.

Results
As illustrated in FIGS. 22A-B, compared to saline injected mice, the cell-transplanted mice show a better performance on rotarod, delayed onset of the disease and increased survival.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of generating astrocyte-like cells expressing glial derived neurotrophic factor (GDNF) at a level at least 2 times greater than a basal production of said GDNF in a non-differentiated mesenchymal stem cell cultured in a serum-free medium, the method comprising:
   (a) culturing mesenchymal stem cells in a medium comprising human epidermal growth factor (hEGF) and human basic fibroblast growth factor (hbFGF), wherein said medium is devoid of PDGF and human neuregulin 1-β1; and subsequently
   (b) incubating said mesenchymal stem cells in a differentiating medium comprising platelet derived growth factor (PDGF) and human neuregulin 1-β1, wherein said differentiating medium is devoid of hbEGF and hEGF, thereby generating astrocyte-like cells that express GDNF at a level at least 2 times greater than a basal production of said GDNF in a non-differentiated mesenchymal stem cell, cultured in a serum-free medium.

2. The method of claim 1, wherein a duration of said incubating is about 48 hours.

3. The method of claim 1, wherein a concentration of said PDGF is about 5 ng/ml.

4. The method of claim 1, wherein a concentration of said human neuregulin 1-β1 is about 50 ng/ml.

5. The method of claim 1, wherein said differentiating medium further comprises L-glutamine, dibutyryl cyclic AMP and isobutylmethylxanthine IBMX.

6. The method of claim 1, wherein a concentration of hEGF is about 20 ng/ml.

7. The method of claim 1, wherein a concentration of hbFGF is about 20 ng/ml.

8. The method of claim 1, wherein said medium further comprises L-glutamine, insulin, progesterone, putrescin, selenium and transferrin.

9. The method of claim 1, wherein a duration of said culturing is about 48 hours.

10. The method of claim 1, wherein said mesenchymal stem cells are obtained by:
    (a) culturing a population of cells comprising said mesenchymal stem cells in a proliferating medium capable of maintaining and/or expanding said mesenchymal stem cells; and
    (b) selecting said mesenchymal stem cells from the cells resulting from step (a).

11. The method of claim 10, wherein step (b) is affected by harvesting surface adhering cells.

12. The method of claim 1, wherein a secretion of said GDNF in the astrocyte-like cells is regulated by IL-1 beta and/or cabergoline.

13. The method of claim 1, wherein the astrocyte-like cells further express glial fibrillary acidic protein (GFAP).

14. The method of claim 1, further comprising isolating said astrocyte-like cells expressing glial derived neurotrophic factor (GDNF).

\* \* \* \* \*

```
                        SEQUENCE LISTING

<160> NUMBER OF SEQ ID NOS: 56

<210> SEQ ID NO 1
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 1
cgacagtcag ccgcatctt                                               19

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
ccaatacgac caaatccgtt g                                            21

<210> SEQ ID NO 3
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 3
tcaaatatgc cagaggatta tcctg                                        25

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
gccatttgtt tatctggtga cctt                                         24

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
agctccgggt tggtatactg g                                            21

<210> SEQ ID NO 6
<211> LENGTH: 20
<212> TYPE: DNA
```

```
<213> ORGANISM: Artificial sequence
<220> FEATURE:
<223> OTHER INFORMATION: Single strand DNA oligonucleotide

<400> SEQUENCE: 6
cctggtggaa cttctttgcg                                              20

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
agaatgagct accgggaagt ca                                           22

<210> SEQ ID NO 8
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 8
ctagcgccgc cattcct                                                 17

<210> SEQ ID NO 9
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 9
catgctggac ccaagctca                                               19

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
gacattacgc tatgcacctc agtg                                         24

<210> SEQ ID NO 11
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 11
tagagggcga ggagaaccg                                               19

<210> SEQ ID NO 12
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 12
gtggccttct gacacagact tg                                           22
```

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
ttggctcaga ggaacccaag                                              20

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
caggatgaca ccaaacaccg t                                            21

<210> SEQ ID NO 15
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 15
gggtgagaca aggaagagga tg                                           22

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
gcttgtgctt gtctccctcc                                              20

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 17
cgaaggcctg cagagacc                                                18

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18
agggtatact cctgctccat gc                                           22

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

```
<400> SEQUENCE: 19
gccctcacac ttgaccagtt                                              20

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
ctagtggacc agagccttcg                                              20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
tgcatgtgca gactcctttc                                              20

<210> SEQ ID NO 22
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 22
aaggagcagg gagcatac                                                18

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
acacagtaag cccaggtagt                                              20

<210> SEQ ID NO 24
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 24
gatgcagaac ttgacaacg                                               19

<210> SEQ ID NO 25
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 25
ttttccactc cagccatcc                                               19

<210> SEQ ID NO 26
<211> LENGTH: 19
<212> TYPE: DNA
```

```
<213> ORGANISM: Artificial sequence
<220> FEATURE:
<223> OTHER INFORMATION: Single strand DNA oligonucleotide

<400> SEQUENCE: 26
ccagaaactc aagcaccac                                                  19

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
ttctcagact tctccaccac                                                 20

<210> SEQ ID NO 28
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 28
aaagcaccaa ggactcact                                                  19

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
gaggcgcacg aagtactcca                                                 20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
gaggggaagg ccgtgctaaa                                                 20

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
ctggctatga ggtcttgttc                                                 20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
ctacggctac taccaggatg                                                 20
```

```
<210> SEQ ID NO 33
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 33
gccatttgtt tatctggtga cctt                                          24

<210> SEQ ID NO 34
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 34
tcaaatatgc cagaggatta tcctg                                         25

<210> SEQ ID NO 35
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 35
gacattacgc tatgcacctc agtg                                          24

<210> SEQ ID NO 36
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 36
catgctggac ccaagctca                                                19

<210> SEQ ID NO 37
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 37
ttgcgttctt caaatgtact tcct                                          24

<210> SEQ ID NO 38
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 38
tcagctcgct ctgtccgtg                                                19

<210> SEQ ID NO 39
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 39
cctggtggaa cttctttgcg                                          20

<210> SEQ ID NO 40
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 40
agctccgggt tggtatactg g                                        21

<210> SEQ ID NO 41
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 41
cccatccgca gagtccag                                            18

<210> SEQ ID NO 42
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 42
cctgactgct cttacggaat cctat                                    25

<210> SEQ ID NO 43
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 43
gtggccttct gacacagact tg                                       22

<210> SEQ ID NO 44
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 44
tagagggcga ggagaaccg                                           19

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
gcttgtgctt gtctccctcc                                          20

<210> SEQ ID NO 46
<211> LENGTH: 22
<212> TYPE: DNA

```
<213> ORGANISM: Artificial sequence
<220> FEATURE:
<223> OTHER INFORMATION: Single strand DNA oligonucleotide

<400> SEQUENCE: 46
gggtgagaca aggaagagga tg                                          22

<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 47
tgccaattca tgttcttccg                                             20

<210> SEQ ID NO 48
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 48
gacttcagag aacaataaac tcgtgg                                      26

<210> SEQ ID NO 49
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 49
ctagcgccgc cattcct                                                17

<210> SEQ ID NO 50
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 50
agaatgagct accgggaagt ca                                          22

<210> SEQ ID NO 51
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 51
agggtatact cctgctccat g                                           21

<210> SEQ ID NO 52
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 52
cgaaggcctg cagagacc                                               18
```

```
<210> SEQ ID NO 53
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 53
caggatgaca ccaaacaccg t                                            21

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
ttggctcaga ggaacccaag                                              20

<210> SEQ ID NO 55
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 55
ccaatacgac caaatccgtt g                                            21

<210> SEQ ID NO 56
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 56
cgacagtcag ccgcatctt                                               19
```